United States Patent

Yano et al.

[11] Patent Number: 6,159,969
[45] Date of Patent: Dec. 12, 2000

[54] URACIL DERIVATIVES, AND ANTITUMOR EFFECT POTENTIATOR AND ANTITUMOR AGENT CONTAINING THE SAME

[75] Inventors: Shingo Yano, Kawagoe; Yukio Tada, Higashimatsuyama; Hideki Kazuno; Tsutomu Sato, both of Hanno; Junichi Yamashita, Honjo; Norihiko Suzuki, Hidaka; Tomohiro Emura, Iruma; Masakazu Fukushima, Hanno; Tetsuji Asao, Tokorozawa, all of Japan

[73] Assignee: Taiho Pharmaceutical Co., Ltd., Tokyo, Japan

[21] Appl. No.: 09/006,009

[22] Filed: Jan. 12, 1998

Related U.S. Application Data

[62] Division of application No. 08/737,677, Nov. 21, 1996, Pat. No. 5,744,475.

[30] Foreign Application Priority Data

Mar. 29, 1995 [JP] Japan ..................... 7-071667

[51] Int. Cl.$^7$ ................. A61K 31/535; C07D 413/00; C07D 401/00; C07D 239/02
[52] U.S. Cl. ............. 514/235.8; 540/598; 544/123; 544/310; 544/311; 544/313
[58] Field of Search ............ 514/235.8; 544/123; 544/310, 311, 313; 540/598

[56] References Cited

U.S. PATENT DOCUMENTS

| | | | |
|---|---|---|---|
| 4,820,712 | 4/1989 | Ottenheijim | 514/274 |
| 5,318,972 | 6/1994 | Miyasaka et al. | 514/269 |
| 5,461,060 | 10/1995 | Miyasaka et al. | 514/269 |
| 5,744,475 | 4/1998 | Yano et al. | 514/274 |

FOREIGN PATENT DOCUMENTS

| | | | |
|---|---|---|---|
| 3279366 | 12/1991 | Japan | C07D 239/47 |
| 3284670 | 12/1991 | Japan | C07D 239/54 |

OTHER PUBLICATIONS

Kinoshita et al, *Journal of Heterocyclic Chemistry*, 29(4):741–747 (1992).

S. Fabrissin et al., "Synthesis and Anticancer Activity of 5–Diethylaminomethyl Derivatives and Nitrogen Mustards of Uracil and 2–Thiouracils", Journal of Medicinal Chemistry, vol. 19, No. 5, 1976 pp. 639–642.

A.A. Ordukhanyan et al., "Study of the Relation Between Structure and Biological Activity. Antineoplastic Activity of Pyrimidine Derivatives", Chemical Abstracts, vol. 92, No. 3, Jan. 21, 1980, p. 25.

I.P. Serzhanin, "Use of Pyrimidines and Adaptogens to Attenuate the Toxic Effect of Tumor Inhibitors" Dec. 4, 1967, Chemical Abstracts, vol. 67, No. 23, p. 10099.

P. Nantka–Namirski, J. Wojciehowski, "Synthesis of 4–methyluracil Derivatives", Acta Poloniae Pharmaceutica, vol. 27, No. 4, 1970, pp. 341–347.

*Primary Examiner*—Mukund J. Shah
*Assistant Examiner*—Tamthom N. Truong
*Attorney, Agent, or Firm*—Sughrue, Mion, Zinn, Macpeak & Seas, PLLC

[57] ABSTRACT

The invention relates to novel uracil derivatives having excellent inhibiting effects of human derived thymidine phosphorylase and anti-tumor activity. The pharmaceutical compositions, anti-tumor potentiators, antitumor agents containing such novel compounds, and a process for their preparation and use is described. The novel compounds satisfy the general formula (1):

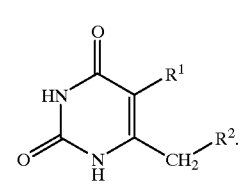

14 Claims, No Drawings

URACIL DERIVATIVES, AND ANTITUMOR EFFECT POTENTIATOR AND ANTITUMOR AGENT CONTAINING THE SAME

This is a Divisional Application of Parent application Ser. No. 08/737,677, filed Nov. 21, 1996 now U.S. Pat. No. 5,744,475.

TECHNICAL FIELD

This invention relates to novel uracil derivatives having excellent inhibitory effects on human-derived thymidine phosphorylase, and also to antitumor effect potentiators and antitumor agents containing same.

BACKGROUND ART

Unnatural pyrimidine nucleosides showing antitumor activities, such as 5-fluoro-2'-deoxyuridine and 5-trifluoromethyl-2'-deoxyuridine, have already known to have strong in vitro activities [Cancer Research, 18, 335 (1958); 22, 815 (1962); 28, 2529 (1968); Proceedings of the Society for Experimental Biology and Medicine, 97, 470 (1958)].

However, these compounds are known to be promptly decomposed and inactivated in vitro by pyrimidine nucleoside phosphorylase which are found in the liver, the small intestine and the like [Cancer Research, 32, 247 (1972); Japanese Journal of Cancer and Chemotherapy, 8, 262 (1981); 8, 1548 (1981)], so that none of them have been found to bring about satisfactory clinical antitumor effects [Cancer Chemotherapy Reports Part 1, 55, 205 (1971); Physicians' Desk Reference, 32, 1387 (1978)].

With a view to preventing the inactivation, research have hence been conducted to develop inhibitors for pyrimidine nucleoside phosphorylase, and some strong inhibitors have been reported. Incidentally, there are two types of pyrimidine nucleoside phosphorylases, that is, uridine phosphorylase and thymidine phosphorylase. It has been reported that uridine phosphorylase is a primary enzyme in selenodonts such as mice and rats while thymidine phosphorylase is a principal enzyme in human and the like [Japanese Journal of Cancer and Chemotherapy, 8, 262 (1981)]. Potentiating the antitumor effects in human therefore requires an inhibitor for thymidine phosphorylase rather than an inhibitor for uridine phosphorylase.

However, a great majority of inhibitors which have been reported to date selectively exhibit inhibitory activities against uridine phosphorylase and show practically no activities against thymidine phosphorylase. Reported to date as exceptions, in other words, as inhibitors for thymidine phosphorylase are 6-amino-5-bromouracil and 6-aminothymine [Biochemical Pharmacology, 29, 1059 (1980)], 6-amino-5-chlorouracil and 3-cyano-2,6-dihydroxypyridine [Japanese Patent Application Laid-Open (Kokai) No. SHO 63-250324], acyclothymidine [Japanese Patent Application Laid-Open (Kokai) No. HEI 5-213761], and the like. Their inhibitory activities are however not sufficient.

Further, human thymidine phosphorylase has recently been found to be the same as PD-ECGF (Platelet Derived Endothelial Cell Growth Factor) which is a human endogenous angiogenic factor [Nature, 356, 668 (1992)]. Accordingly, a thymidine phosphorylase inhibitor can inhibit angiogenesis which is closely associated with malignancy of pathomas such as solid tumors, rheumatism and diabetic retinopathy, and is useful as a therapeutic for these diseases.

In addition, 5-trifluoromethyl-2'-deoxyuridine also has antiviral activities and is used as an eye drop for herpetic keratitis [Science, 145 (3632), 585 (1964); American Journal of Ophthalmology, 73, 932 (1972)]. Phosphorylase inhibitors are also expected to have utility as enhancers for antiviral activities and effects.

An object of the present invention is therefore to provide a novel compound which has excellent inhibitory effects on human-derived thymidine phosphorylase and is useful as an antitumor effect potentiator and an antitumor agent.

With the foregoing circumstances in view, the present inventors have proceeded with extensive research. As a result, it has been found that a uracil derivative represented by the below-described formula (1) has excellent inhibitor effects on human-derived thymidine phosphorylase, leading to the completion of the present invention.

DISCLOSURE OF THE INVENTION

This invention relates to a uracil derivative represented by the following formula (1'):

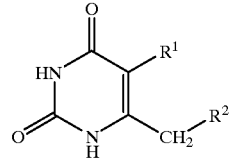

(1')

wherein $R^1$ represents a chlorine, bromine or iodine atom or a cyano or lower alkyl group; and $R^2$ represents a 4–8 membered heterocyclic group having 1–3 nitrogen atoms, which may be substituted by one or more lower alkyl, imino, hydroxyl, hydroxymethyl, methanesulfonyloxy, amino or nitro groups; an amidinothio group, one or more of the hydrogen atom(s) on one or both of the nitrogen atoms of which may each be substituted by a lower alkyl group; a guanidino group, one or more of the hydrogen atom(s) on one, two or all of the nitrogen atoms of which may each be substituted by a lower alkyl or cyano group; a (lower alkyl)amidino group; an amino group, one or both of the hydrogen atoms on the nitrogen atom of which may each be substituted by a lower alkyl group; a group —$CH_2N(R^a)R^b$ in which $R^a$ and $R^b$ may be the same or different and each represents a hydrogen atom or a lower alkyl group or $R^a$ and $R^b$ may form a pyrrolidine ring together with the nitrogen atom to which $R^a$ and $R^b$ are bonded; a group —NH—$(CH_2)_m$—Z in which Z represents an amino group, one or both of the hydrogen atoms on the nitrogen atom of which may each be substituted by a lower alkyl group, or a cyano group, and m stands for an integer of from 0 to 3; a group $NR^c(CH_2)_n$—OH in which $R^c$ represents a hydrogen atom or a lower alkyl group, and n stands for a natural number of from 1 to 4; a group —X—Y in which X represents S or NH, and Y represents a 2-imidazolin-2-yl, 2-imidazolyl, 1-methylimidazol-2-yl, 1,2,4-triazol-3-yl, 2-pyrimidyl or 2-benzimidazolyl group which may be substituted by one or more lower alkyl groups; or a ureido or thioureido group, one or more of the hydrogen atom(s) on one or both of the nitrogen atoms of which may each be substituted by a lower alkyl group, with the proviso that $R^1$ and $R^2$ are not a bromine atom and an amino group, respectively, at the same time; or a salt thereof.

With respect to 5-bromo-4-aminomethyluracil which has a bromine atom as $R^1$ and an amino group as $R^2$ in the formula (1'), a synthesis process of its hydrochloride salt has been reported [Acta Poloniae Pharmaceutica, 27(4), 329 (1970)], but its inhibitory effects on human-derived thymidine phosphorylase have not been known.

Accordingly, the present invention relates to a pharmaceutical comprising, as an active ingredient, a uracil derivative represented by the following formula (1):

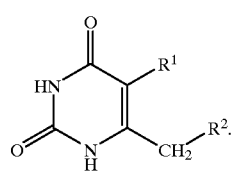

(1)

wherein $R^1$ represents a chlorine, bromine or iodine atom or a cyano or lower alkyl group; and $R^2$ represents a 4–8 membered heterocyclic group having 1–3 nitrogen atoms, which may be substituted by one or more lower alkyl, imino, hydroxyl, hydroxymethyl, methanesulfonyloxy, amino or nitro groups; an amidinothio group, one or more of the hydrogen atom(s) on one or both of the nitrogen atoms of which may each be substituted by a lower alkyl group; a guanidino group, one or more of the hydrogen atom(s) on one, two or all of the nitrogen atoms of which may each be substituted by a lower alkyl or cyano group; a (lower alkyl)amidino group; an amino group, one or both of the hydrogen atoms on the nitrogen atom of which may each be substituted by a lower alkyl group; a group —$CH_2N(R^a)R^b$ in which $R^a$ and $R^b$ may be the same or different and each represents a hydrogen atom or a lower alkyl group or $R^a$ and $R^b$ may form a pyrrolidine ring together with the nitrogen atom to which $R^a$ and $R^b$ are bonded; a group —NH—$(CH_2)_m$—Z in which Z represents an amino group, one or both of the hydrogen atoms on the nitrogen atom of which may each be substituted by a lower alkyl group, or a cyano group, and m stands for an integer of from 0 to 3; a group $NR^c(CH_2)_n$—OH in which $R^c$ represents a hydrogen atom or a lower alkyl group, and n stands for a natural number of from 1 to 4; a group —X—Y in which X represents S or NH, and Y represents a 2-imidazolin-2-yl, 2-imidazolyl, 1-methylimidazol-2-yl, 1,2,4-triazol-3-yl, 2-pyrimidyl or 2-benzimidazolyl group which may be substituted by one or more lower alkyl groups; or a ureido or thioureido group, one or more of the hydrogen atom(s) on one or both of the nitrogen atoms of which may each be substituted by a lower alkyl group; or a salt thereof.

The present invention also relates to an antitumor effect potentiator for an antitumor agent containing a 2'-deoxypyrimidine nucleoside, which comprises as an active ingredient the uracil derivative represented by the formula (1) or the salt thereof.

In addition, the present invention is concerned with an antitumor agent comprising the uracil derivative represented by the formula (1) or the salt thereof and a 2'-deoxypyrimidine nucleoside.

The present invention is also concerned with a pharmaceutical composition comprising the uracil derivative represented by the formula (1) or the salt thereof and a pharmaceutically acceptable carrier.

The present invention is also concerned with an antitumor agent comprising the uracil derivative represented by the formula (1) or the salt thereof, a 2'-deoxypyrimidine nucleoside and a pharmaceutically acceptable carrier.

Further, the present invention pertains to use of the uracil derivative represented by the formula (1) or the salt thereof as a pharmaceutical.

The present invention also pertains to use of the uracil derivative represented by the formula (1) or the salt thereof as an antitumor effect potentiator for an antitumor agent containing a 2'-deoxypyrimidine nucleoside.

The present invention also pertains to use of the uracil derivative represented by the formula (1) or the salt thereof for the production of an antitumor agent comprising the uracil derivative represented by the formula (1) or the salt thereof and a 2'-deoxypyrimidine nucleoside.

Moreover, the present invention relates to a method for potentiating antitumor effect of an antitumor agent containing a 2'-deoxypyrimidine nucleoside, which comprises administering to a patient an effective amount of the uracil derivative represented by formula (1) or the salt thereof.

The present invention also relates to a therapeutic method of a cancer, which comprises administering to a patient effective amounts of the uracil derivative represented by formula (1) or the salt thereof and a 2'-deoxypyrimidine nucleoside.

BEST MODE FOR CARRYING OUT THE INVENTION

Illustrative of the lower alkyl group represented by $R^1$ and $R^2$ in the formulas (1) and (1') are linear or branched alkyl groups having 1 to 4,carbon atoms. Specific examples include methyl, ethyl, n-propyl, i-propyl, n-butyl, i-butyl, sec-butyl and t-butyl groups. Among these, a methyl group is particularly preferred.

Illustrative of the 4–8 membered heterocyclic group containing 1–3 nitrogen atoms and represented by $R^2$ are 1-azetidinyl, 1-pyrrolidinyl, 2-pyrrolin-1-yl, 3-pyrrolin-1-yl, 1-pyrrolyl, 1-pyrazolidinyl, 2-pyrazolin-1-yl, 3-pyrazolin-1-yl, 4-pyrazolin-1-yl, 1-pyrazolyl, 1-imidazolidinyl, 2-imidazolin-1-yl, 3-imidazolin-1-yl, 4-imidazolin-1-yl, 1-imidazolyl, 1,2,3-triazol-1-yl, 1,2,4-triazol-1-yl, piperidino, 1-piperazyl, morpholino, 1-perhydroazepinyl and 1-perhydroazocinyl groups. Further, these heterocyclic groups may contain one or two substituent groups on their rings. Examples of such substituent groups include lower alkyl, imino, hydroxyl, hydroxymethyl, methanesulfonyloxy, amino and nitro groups. Specific examples of the heterocyclic group which may contain such substituent groups include 1-azetidinyl, 1-pyrrolidinyl, 2,5-dimethylpyrrolidin-1-yl, 2-iminopyrrolidin-1-yl, 3-hydroxypyrrolidin-1-yl, 2-hydroxymethylpyrrolidin-1-yl, 3-methanesulfonyloxypyrrolidin-1-yl, 3-aminopyrrolidin-1-yl, 2-pyrrolin-1-yl, 3 -pyrrolin-1-yl, 2-imino-3-pyrrolin-1-yl, 1-pyrrolyl, 1-pyrazolidinyl, 2-methylpyrazolidin-1-yl, 4-iminopyrazolidin-1-yl, 2-pyrazolin-1-yl, 3-pyrazolin-1-yl, 2-methyl-3-pyrazolin-1-yl, 5-imino-3-pyrazolin-1-yl, 4-pyrazolin-1-yl, 2-methyl-4-pyrazolin-1-yl, 3-imino-4-pyrazolin-1-yl, 1-pyrazolyl, 1-imidazolidinyl, 3-methylimidazolidin-1-yl, 2-iminoimidazolidin-1-yl, 2-imino-3-methylimidazolidin-1-yl, 2-imino-3-ethylimidazolidin-1-yl, 2-imino-3-isopropylimidazolidin-1-yl, 2-imidazolin-1-yl, 3-imidazolin-1-yl, 4-imidazolin-1-yl, 3-methyl-4-imidazolin-1-yl, 2-imino-4-imidazolin-1-yl, 2-imino-3-methyl-4-imidazolin-1-yl, 2-imino-3-ethyl-4-imidazolin-1-yl, 2-imino-3-isopropyl-4-imidazolin-1-yl, 1-imidazolyl, 2-methylimidazol-1-yl, 2-nitroimidazol-1-yl, 4-nitroimidazol-1-yl, 1,2,3-triazol-1-yl, 1,2,4-triazol-1-yl, 3-nitro-1,2,4-triazol-1-yl, piperidino, 1-piperazyl, 4-methylpiperazin-1-yl, morpholino, 1-perhydroazepinyl and 1-perhydroazocinyl groups. Preferred examples include 1-azetidinyl, 1-pyrrolidinyl, 2-iminopyrrolidin-1-yl, 2-iminoimidazolidin-1-yl, 2-imino-3-methylimidazolidin-1-yl, 2-imino-3-ethylimidazolidin-1-yl, 2-imino-3- isopropylimidazolidin-1-yl, 2-imidazolin-1-yl, 2-imino-3-methyl-4-imidazolin-1-yl, 2-.imino-3-ethyl-4-imidazolin-1-yl and 1-imidazolyl groups.

Illustrative of the amidinothio group represented by $R^2$, one or more of the hydrogen atom(s) on one or both of the nitrogen atoms of which may each be substituted by a lower alkyl group, are those in which one to three of the three hydrogen atoms on the nitrogen atoms of an amidino group may be substituted by the above lower alkyl group or groups. Especially, amidinothio, $N^1$-methylamidinothio and $N^1,N^2$-dimethylamidinothio groups are preferred.

Illustrative of the guanidino group, one or more of the hydrogen atom(s) on one, two or all of the nitrogen atoms of which may each be substituted by a lower alkyl or cyano group, are those in each of which one to four of the four hydrogen atoms in a guanidino group may be substituted by the above lower alkyl or cyano group or groups. Especially, 1-guanidino, 1-methylguanidino, 3-methylguanidino, 2,3-dimethylguanidino and 2-cyano-3-methylguanidino groups are preferred.

Illustrative of the (lower alkyl)amidino group are those formed of amidino groups and the lower alkyl groups bonded thereto, respectively. Of these, an acetoamidino group is preferred.

Illustrative of the amino group, one or both of the hydrogen atoms on the nitrogen atom of which may each be substituted by a lower alkyl group, are those in each of which one or two of the two hydrogen atoms on an amino group may be substituted by the above lower alkyl group or groups. Of these, amino, N-methylamino, N,N-dimethylamino, N-ethylamino, N,N-diethylamino, N-propylamino and N-isopropylamino groups are preferred.

Preferred examples of the group represented by —$CH_2N(R^a)R^b$ include N-methylaminomethyl, N,N-dimethylaminomethyl and 1-pyrrolidinylmethyl groups.

Preferred examples of the group represented by —NH—$(CH_2)_m$—Z include N,N-dimethylhydrazino, N-(2-aminoethyl)amino, N-(2-(N,N-dimethyl)aminoethyl)amino, N-(3-aminopropyl)amino and N-(2-cyanoethyl)amino groups.

Preferred examples of the group $NR^c(CH_2)_n$—OH include N-(2-hydroxyethyl)-N-methylamino, N-(3-hydroxypropyl)amino and N-(4-hydroxybutyl)amino groups.

Preferred examples of the group represented by —X—Y include 2-imidazolin-2-thio, 2-imidazolin-2-amino, imidazol-2-thio, 1-methylimidazol-2-thio, 1,2,4-triazol-3-thio, pyrimidin-2-thio and benzimidazol-2-thio groups.

Preferred examples of the ureido or thioureido group, one or more of the hydrogen atom(s) on one or both of the nitrogen atoms of which may each be substituted by a lower alkyl group, include ureido and 3-methylthioureido groups.

Preferred examples of the group represented by $R^2$ in the formula (1) include 4–8 membered heterocyclic groups having 1–3 nitrogen atoms, which may each be substituted by one or more lower alkyl, imino, hydroxyl, hydroxymethyl, methanesulfonyloxy, amino or nitro groups; amidinothio groups, one or more of the hydrogen atom(s) on one or both of the nitrogen atoms of each of which may each be substituted by a lower alkyl group; guanidino groups, one or more of the hydrogen atom(s) on one, two or all of the nitrogen atoms of each of which may each be substituted by a lower alkyl or cyano group; or (lower alkyl)amidino groups.

Among the groups represented by $R^2$, preferred specific examples include 1-azetidinyl, 1-pyrrolidinyl, 2-iminopyrrolidin-1-yl, 2-iminoimidazolidin-1-yl, 2-imino-3-methylimidazolidin-1-yl, 2-imino-3-ethylimidazolidin-1-yl, 2-imino-3-isopropylimidazolidin-1-yl, 2-imidazolin-1-yl, 2-imino-3-methyl-4-imidazolin-1-yl, 2-imino-3-ethyl-4-imidazolin-1-yl, 1-imidazolyl, amidinothio, $N^1$-methylamidinothio, $N^1,N^2$-dimethylamidinothio, 1-guanidino, 1-methylguanidino, 3-methylguanidino, 2,3-dimethylguanidino and acetoamidino groups.

Preferred examples of the uracil derivative represented by the formula (1) include those containing a chlorine or bromine atom or a cyano group as $R^1$ and a 1-pyrrolidinyl, 1-azetidinyl, 2-iminopyrrolidin-1-yl, 2-iminoimidazolidin-1-yl, 1-imidazolyl, amidinothio or 1-guanidino group as $R^2$.

Examples of the salt of the uracil derivative (1) can include, but are not limited to, acid-addition salts and/or base salts which have been obtained by causing pharmacologically acceptable acids or basic compounds to act respectively. Examples of these acid addition salts include salts with inorganic acids such as hydrochloric acid, sulfuric acid, phosphoric acid and hydrobromic acid as well as salts with organic acids such as oxalic acid, maleic acid, fumaric acid, malic acid, tartaric acid, citric acid, benzoic acid, acetic acid, p-toluenesulfonic acid and methanesulfonic acid, with the salt with hydrochloric acid or p-toluenesulfonic acid being preferred. Exemplary base salts include salts with alkali metals and alkaline earth metals such as sodium, potassium, magnesium and calcium as well as salts with amines such as ammonia, methylamine, dimethylamine, piperidine, cyclohexylamine and triethylamine.

Particularly preferred specific examples of the uracil derivative (1) or its salt include:

5-chloro-6-(1-pyrrolidinylmethy)uracil, 5-bromo-6-(1-pyrrolidinylmethyl)uracil, 5-chloro-6-(1-azetidinylmethyl)uracil, 5-chloro-6-(1-(2-iminopyrrolidinyl)methyl)uracil hydrochloride, 5-bromo-6-(1-(2-iminopyrrolidinyl)methyl)uracil hydrochloride, 5-cyano-6-(1-(2-iminopyrrolidinyl)methyl)uracil, 5-chloro-6-(1-(2-iminoimidazolidinyl)methyl) uracil, 5-bromo-6-(1-(2-iminoimidazolidinyl)methyl) uracil, 5-chloro-6-(1-imidazolylmethyl)uracil hydrochloride, 2-(5-chlorouracil-6-ylmethyl)isothiourea hydrochloride, 2-(5-cyanouracil-6-ylmethyl)isothiourea hydrochloride, 5-chloro-6-(1-guanidino)methyluracil hydrochloride.

The uracil derivative (1) of the present invention can be prepared, for instance, in accordance with the following Processes A to M, using various compounds as raw materials:

[Process A]

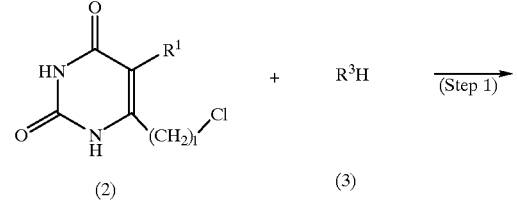

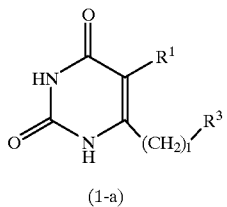

(1-a)

wherein $R^1$ has the same meaning as defined above, l stands for a number of 1 or 2, and $R^3$ represents 4–8 membered heterocyclic group having 1–3 nitrogen atoms, which may be substituted by one or more lower alkyl, imino, hydroxyl, hydroxymethyl, amino or nitro groups; a group —NH—$(CH_2)_m$—Z in which Z represents an amino group, one or both of the hydrogen atoms on the nitrogen atom of which may each be substituted by a lower alkyl group, or a cyano group, and m stands for an integer of from 0 to 3; or a group $NR^c(CH_2)_n$—OH in which $R^c$ represents a hydrogen atom or a lower alkyl group, and n stands for a natural number of from 1 to 4.

(Step 1)

The compound represented by the formula (1-a) can be prepared by reacting the compound represented by the formula (2), which is obtained by the below-described preparation processes (Process N) and (Process O), and the known compound represented by the formula (3), which is disclosed in literature [Journal of Organic Chemistry, 32, 738 (1967); Journal of Medicinal Chemistry, 15, 415 (1972)] in a suitable solvent in the presence or absence of a basic compound.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; amines such as pyridine and triethylamine; alkyl ketones such as acetone, methyl ethyl ketone and methyl isobutyl ketone; alcohols such as methanol, ethanol and propanol; and water.

Illustrative basic compounds include organic basic compounds, e.g., tertiary amines such as triethylamine, diisopropylethylamine, tributylamine, pyridine, dimethylaminopyridine and 1,8-diazabicyclo-[5.4.0]undec-7-ene; and inorganic basic compounds, e.g., alkali metal carbonates such as sodium carbonate and potassium carbonate, alkali metal bicarbonates such as sodium bicarbonate and potassium bicarbonate, alkali metal hydroxides such as sodium hydroxide and potassium hydroxide, alkali metals such as sodium and potassium, alkali metal alkoxides such as sodium methoxide, sodium ethoxide and potassium t-butoxide, and alkali metal hydrides such as sodium hydride.

As proportions of the raw materials, it is preferred to use the compound of the formula (3) in an amount of from 1 to 10 mole equivalents, preferably from 1 to 5 mole equivalents and the basic compound in an amount of from 1 to 5 mole equivalents, both per mole of the compound of the formula (2). The reaction temperature may range from 0° C. to the boiling point of the solvent or so, preferably from 0° C. to 80° C. The reaction time may range from 0.1 to 48 hours, preferably from 0.5 to 24 hours.

When $R^3$ is a heterocycle having a hydroxyl group in the compound represented by the formula (1-a), the hydroxyl group can be converted further into a methanesulfonyloxy group by a usual method. Described specifically, the methanesulfonyloxy derivative can be obtained by using N,N-dimethylformamide, dimethylsulfoxide, dichloromethane, pyridine or the like as a solvent, triethylamine, pyridine, dimethylaminopyridine or the like as a basic compound and methanesulfonyl chloride as a mesylating agent, employing the mesylating agent in an amount of from 1 to 2 mole equivalents and the basic compound in an amount of from 1 to 5 mole equivalents, both per mole of the compound of the formula (1-a), and reacting them at a reaction temperate of from 0° C. to the boiling point of the solvent or so for 0.5 to 48 hours.

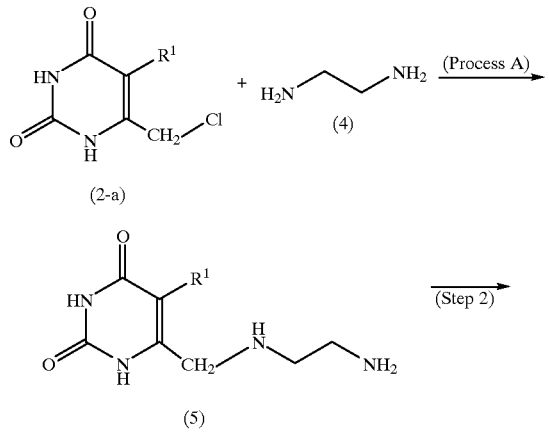

[Process B]

-continued

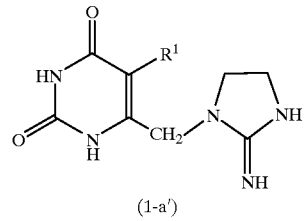

(1-a')

wherein $R^1$ has the same meaning as defined above.

More specifically, the step shown in the above reaction formula can be practiced as will be described hereinafter.
(Step 2)

The compound represented by the formula (1-a') can be prepared by reacting the compound represented by the formula (5), which is obtained by reacting the compound of the formula (2-a) and ethylenediamine (4) in accordance with Process A, with cyanogen bromide in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; alcohols such as methanol, ethanol and propanol; and water.

In this reaction, it is preferred to conduct the reaction by using cyanogen bromide in an amount of from 1 to 2 mole equivalents per mole of the compound of the formula (5). The reaction temperature may range from 0° C. to the boiling point of the solvent or so, preferably from 0° C. to 80° C. The reaction time may range from 0.5 to 48 hours, preferably from 1 to 24 hours.

[Process C]

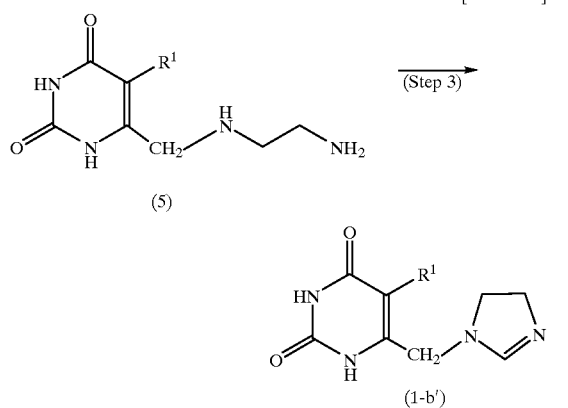

wherein $R^1$ has the same meaning as defined above.

More specifically, the step shown in the above reaction formula can be practiced as will be described hereinafter.
(Step 3)

The compound represented by the formula (1-b') can be prepared by reacting the compound represented by the formula (5) with trimethyl orthoformate in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; alcohols such as methanol, ethanol and propanol; and acetic acid, formic acid and water.

In this reaction, it is preferred to use the trimethyl orthoformate in an amount of from 1 to 2 mole equivalents per mole of the compound of the formula (5). The reaction temperature may range from 0° C. to the boiling point of the solvent or so, preferably from 80° C. to 130° C. The reaction time may range from 0.5 to 12 hours, preferably from 1 to 4 hours.

[Process D]

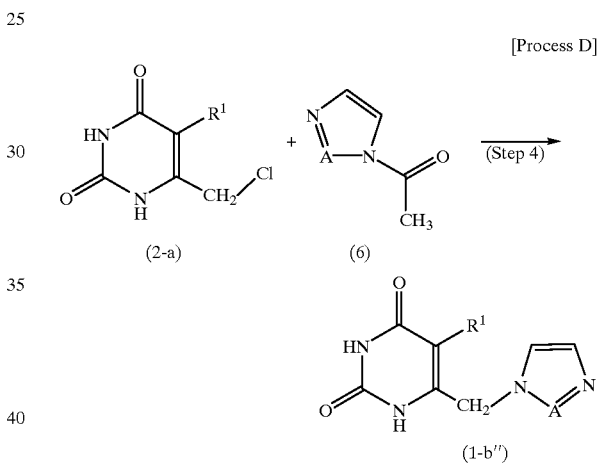

wherein $R^1$ has the same meaning as defined above, and A represents CH or N.

More specifically, the step shown in the above reaction formula can be practiced as will be described hereinafter.
(Step 4)

The compound represented by the formula (1-b") can be prepared by reacting the compound represented by the formula (2-a) with the compound represented by the formula (6) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; alkyl ketones such as acetone, methyl ethyl ketone and methyl isobutyl ketone; alcohols such as methanol, ethanol and propanol; and water.

In this reaction, it is preferred to use the compound of the formula (6) in an amount of from 1 to 2 mole equivalents per mole of the compound of the formula (2-a). The reaction temperature may range from 0° C. to the boiling point of the solvent or so, preferably from 50° C. to 120° C. The reaction time may range from 0.5 to 72 hours, preferably from 1 to 48 hours.

[Process E]

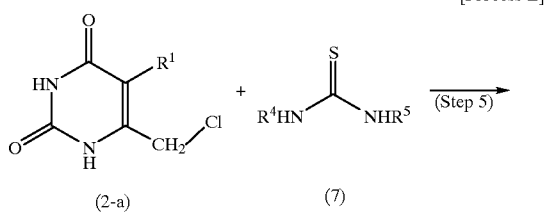

(2-a)  (7)

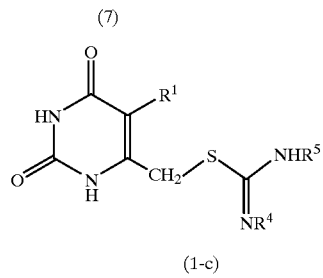

(1-c)

wherein $R^1$ has the same meaning as defined above, and $R^4$ and $R^5$ may be the same or different and each represents a hydrogen atom or a lower alkyl group.

More specifically, the step shown in the above reaction formula can be practiced as will be described hereinafter.

(Step 5)

The compound represented by the formula (1-c) can be prepared by reacting the compound represented by the formula (2-a) with the commercially-available compound represented by the formula (7) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; alkyl ketones such as acetone, methyl ethyl ketone and methyl isobutyl ketone; alcohols such as methanol, ethanol and propanol; and water.

For this reaction, it is preferred to use the compound of the formula (7) in an amount of from 1 to 2 mole equivalents per mole of the compound of the formula (2-a). The reaction temperature may range from 0° C. to the boiling point of the solvent or so, preferably from 50° C. to 120° C. The reaction time may range from 0.5 to 24 hours, preferably from 1 to 8 hours.

[Process F]

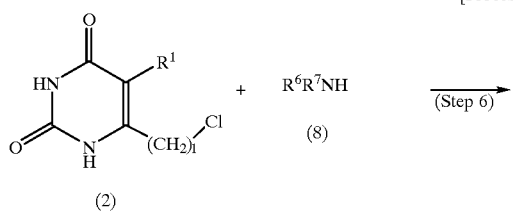

(2)  (8)

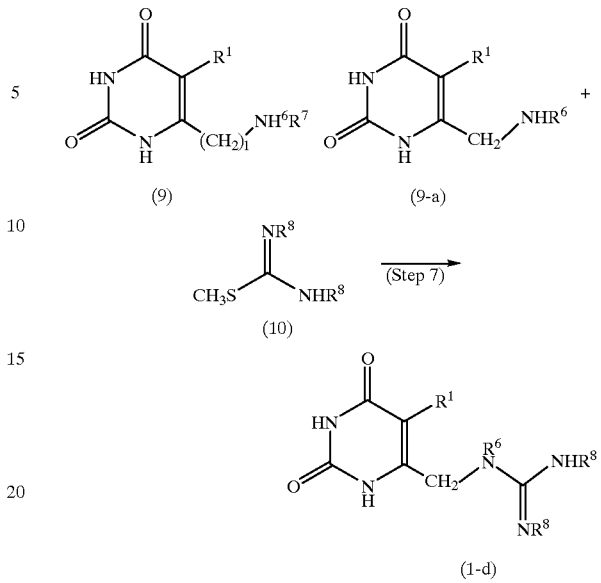

wherein $R^1$ and l have the same meanings as defined above, $R^6$ and $R^7$ may be the same or different and each represents a hydrogen atom or a lower alkyl group, and $R^8$s each represents a hydrogen atom or a lower alkyl group or two $R^8$s represents a 2-imidazolin-2-yl group together with the nitrogen atom to which they are bonded.

More specifically, the individual steps shown in the above reaction scheme can be practiced as will be described hereinafter.

(Step 6)

The compound represented by the formula (9) can be prepared by reacting the compound represented by the formula (2) with the commercially-available compound represented by the formula (8) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as tetrahydrofuran and dioxane; alcohols such as methanol, ethanol and propanol; and water.

In this reaction, it is preferred to use the compound of the formula (8) in an amount of from 1 to 50 mole equivalents, preferably from 1 to 10 mole equivalents per mole of the compound of the formula (2). The reaction temperature may range from 0° C. to the boiling point of the solvent or so, preferably from 0° C. to 80° C. The reaction time may range from 0.5 to 168 hours, preferably from 1 to 96 hours.

The compound of the formula (9) available by the above reaction can be used in Step 7 with or without isolation.

(Step 7)

The compound represented by the formula (1-d) can be prepared by reacting the compound represented by the formula (9-a) and the known compound represented by the formula (10), which is disclosed in literature [Analytical Biochemistry, 57, 310 (1974)] or is commercially available, in a suitable solvent in the presence or absence of a basic compound.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide;

ethers such as tetrahydrofuran and dioxane; alcohols such as methanol, ethanol and propanol; and water.

Illustrative basic compounds include inorganic basic compounds, e.g., alkali metal carbonates such as sodium carbonate and potassium carbonate, alkali metal bicarbonates such as sodium bicarbonate and potassium bicarbonate, alkali metal hydroxides such as sodium hydroxide and potassium hydroxide, alkali metals such as sodium and potassium, alkali metal alkoxides such as sodium methoxide, sodium ethoxide and potassium t-butoxide, and alkali metal hydrides such as sodium hydride.

In this reaction, it is preferred to use the compound of the formula (10) in an amount of from 1 to 2 mole equivalents and the basic compound in an amount of from 1 to 5 mole equivalents, both per mole of the compound of the formula (9-a). The reaction temperature may range from 0° C. to the boiling point of the solvent or so, preferably from 0° C. to 80° C. The reaction time may range from 0.5 to 48 hours, preferably from 1 to 24 hours.

[Process G]

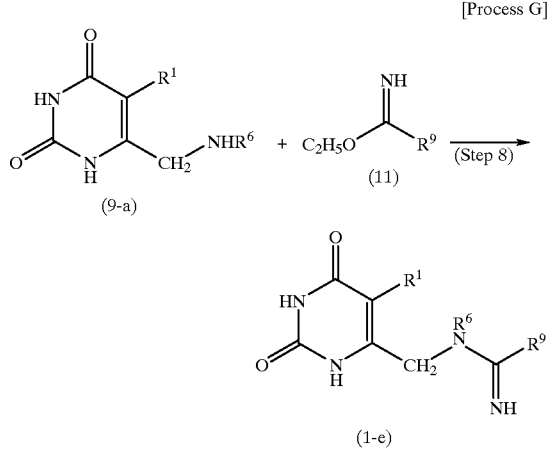

wherein $R^1$ and $R^6$ have the same meanings as defined above, and $R^9$ represents a lower alkyl group.

More specifically, the step shown in the above reaction formula can be practiced as will be described hereinafter.

(Step 8)

The compound represented by the formula (1-e) can be prepared by reacting the compound represented by the formula (9-a) and the compound represented by the formula (11), which is disclosed in literature [Organic Syntheses Collective, 1, 5 (1941)], in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as tetrahydrofuran and dioxane; alcohols such as methanol, ethanol and propanol; and water.

In this reaction, it is preferred to use the compound of the formula (11) in an amount of from 1 to 2 mole equivalents per mole of the compound of the formula (9-a). The reaction temperature may range from 0° C. to the boiling point of the solvent or so, preferably from 0° C. to 80° C. The reaction time may range from 0.5 to 48 hours, preferably from 1 to 24 hours.

[Process H]

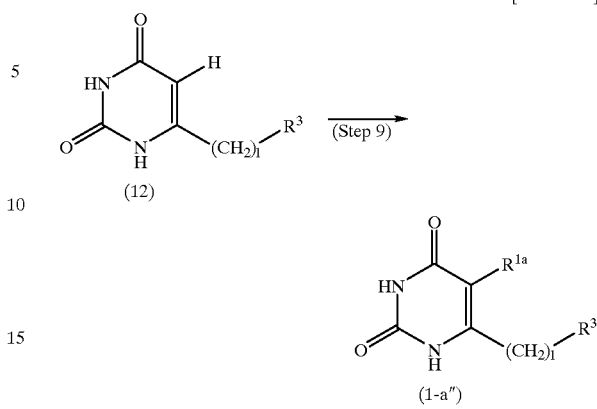

wherein $R^{1a}$ represents a chlorine, bromine or iodine atom, and $R^3$ and l have the same meanings as defined above.

More specifically, the step shown in the above reaction formula can be practiced as will be described hereinafter.

(Step 9)

The compound represented by the formula (1-a″) can be prepared by reacting the compound represented by the formula (12), which is obtained in accordance with the below-described preparation process (Process P), with a chlorinating agent, brominating agent or iodating agent in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as tetrahydrofuran and dioxane; alcohols such as methanol, ethanol and propanol; and acetic acid, formic acid, concentrated sulfuric acid and water.

Illustrative of the chlorinating agent are chlorine, N-chlorosuccinimide, sulfuryl chloride and sodium hypochlorite.

Illustrative of the brominating agent are bromine, N-bromosuccinimide and pyridiniumbromide perbromide.

Illustrative of the iodating agent are iodine ad N-iodosuccinimide.

In this reaction, it is preferred to use the chlorinating agent, brominating agent or iodating agent in an amount of from 1 to 3 mole equivalents per mole of the compound of the formula (12). The reaction temperature may range from 0° C. to the boiling point of the solvent or so, preferably from 0° C. to 80° C. The reaction time may range from 0.5 to 48 hours, preferably from 1 to 12 hours.

[Process I]

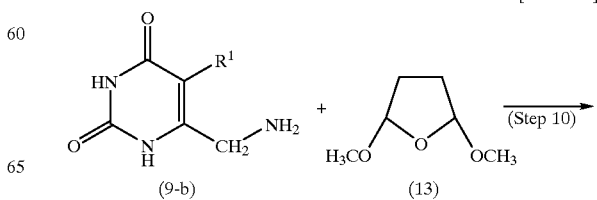

-continued

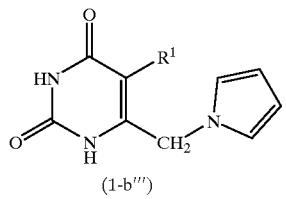

(1-b''')

wherein $R^1$ has the same meaning as defined above.

More specifically, the step shown in the above reaction formula can be practiced as will be described hereinafter.

(Step 10)

The compound represented by the formula (1-b''') can be prepared by reacting the compound represented by the formula (9-b) and 2,5-dimethoxytetrahydrofuran (13) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; alcohols such as methanol, ethanol and propanol; and acetic acid, formic acid, concentrated sulfuric acid and water.

In this reaction, it is preferred to use 2,5-dimethoxytetrahydrofuran (13) in an amount of from 1 to 5 mole equivalents, preferably from 1 to 2 mole equivalents per mole of the compound of the formula (9-b). The reaction temperature may range from 0° C. to the boiling point of the solvent or so, preferably from 0° C. to 120° C. The reaction time may range from 0.5 to 48 hours, preferably from 1 to 24 hours.

[Process J]

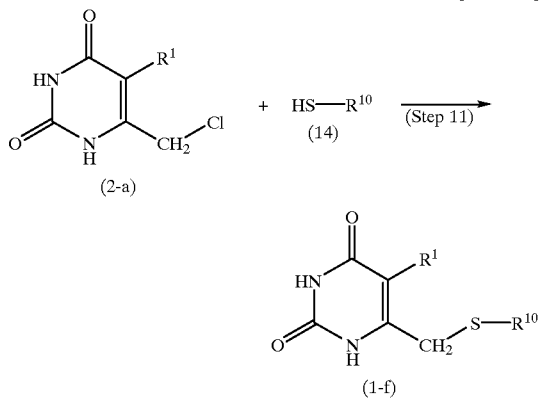

wherein $R^1$ has the same meaning as defined above, and $R^{10}$ represents a 2-imidazolin-2-yl, 2-imidazolyl, 1,2,4-triazol-3-yl, 1-methylimidazol-2-yl, 2-pyrimidyl or 2-benzimidazolyl group.

More specifically, the step shown in the above reaction formula can be practiced as will be described 5 hereinafter.

(Step 11)

The compound represented by the formula (1-f) can be prepared by reacting the compound represented by the formula (2-a) and the commercially-available compound represented by the formula (14) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; alkyl ketones such as acetone, methyl ethyl ketone and methyl isobutyl ketone; alcohols such as methanol, ethanol and propanol; and water.

In this reaction, it is preferred to use the compound of the formula (14) in an amount of from 1 to 3 mole equivalents per mole of the compound of the formula (2-a). The reaction temperature may range from 0° C. to the boiling point of the solvent or so, preferably from 0° C. to 100° C. The reaction time may range from 0.5 to 24 hours, preferably from 1 to 8 hours.

[Process K]

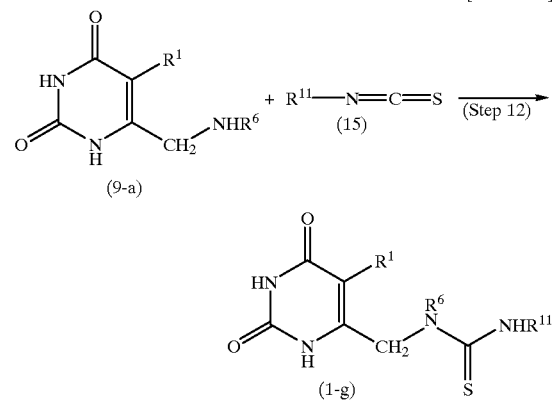

wherein $R^1$ and $R^6$ have the same meanings as defined above, and $R^{11}$ represents a lower alkyl group.

More specifically, the step shown in the above reaction formula can be practiced as will be described hereinafter.

(Step 12)

The compound represented by the formula (1-g) can be prepared by reacting the compound represented by the formula (1-g) and the compound represented by the formula (15) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; and ethers such as tetrahydrofuran and dioxane.

In this reaction, it is preferred to use the compound of the formula (15) in an amount of from 1 to 2 mole equivalents per mole of the compound of the formula (9-a). The reaction temperature may range from 0° C. to the boiling point of the solvent or so, preferably from 0° C. to 80° C. The reaction time may range from 0.5 to 48 hours, preferably from 1 to 24 hours.

[Process L]

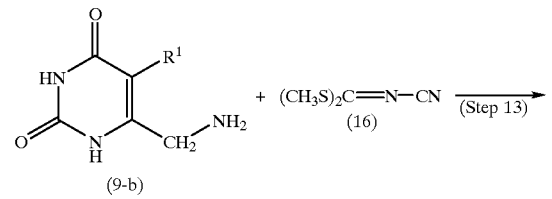

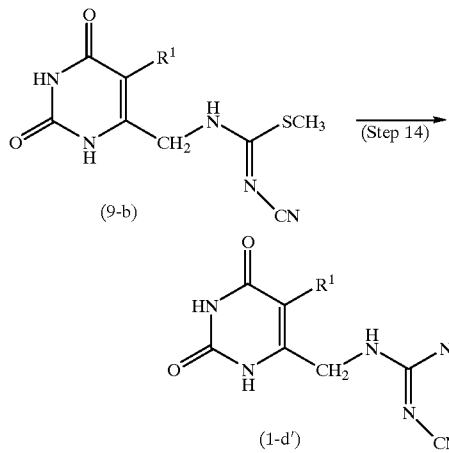

(9-b)

(Step 14) →

(1-d')

wherein $R^1$ has the same meaning as defined above.

More specifically, the step shown in the above reaction formula can be practiced as will be described hereinafter.

(Step 13)

The compound represented by the formula (17) can be prepared by reacting the compound represented by the formula (9-b) and S,S'-dimethyl N-cyanodithioiminocarbonate (16), which is a compound commercially available on the market, in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; amines such as pyridine and triethylamine; alkyl ketones such as acetone, methyl ethyl ketone and methyl isobutyl ketone; alcohols such as methanol, ethanol and propanol; and water.

In this reaction, it is preferred to use S,S'-dimethyl N-cyanodithioiminocarbonate (16) in an amount of from 1 to 5 mole equivalents, preferably from 1 to 2 mole equivalents per mole of the compound of the formula (9-b). The reaction temperature may range from 0° C. to the boiling point of the solvent or so, preferably from 60° C. to 130° C. The reaction time may range from 0.5 to 24 hours, preferably from 1 to 8 hours.

The compound of the formula (17) available by the above reaction can be used in Step 14 with or without isolation.

(Step 14)

The compound represented by the formula (1-d') can be prepared by reacting the compound represented by the formula (17) and methylamine in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; alcohols such as methanol, ethanol and propanol; and water.

In this reaction, it is preferred to use methylamine in an amount of from 1 to 100 mole equivalents per mole of the compound of the formula (17). The reaction temperature may range from 0° C. to the boiling point of the solvent or so, preferably from 0° C. to 80° C. The reaction time may range from 0.5 to 24 hours, preferably from 1 to 8 hours.

[Process M]

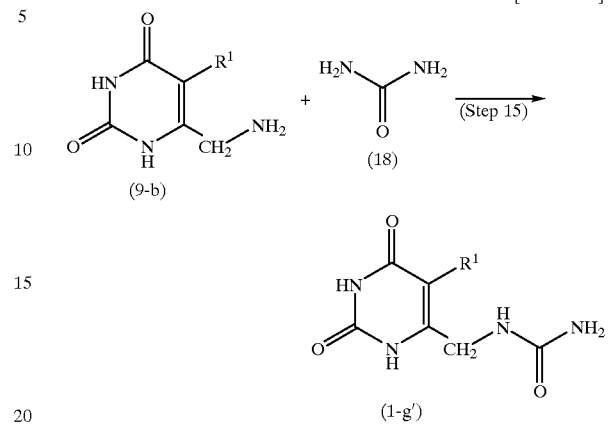

(9-b) + (18) (Step 15) →

(1-g')

wherein $R^1$ has the same meaning as defined above.

More specifically, the step shown in the above reaction formula can be practiced as will be described hereinafter.

(Step 15)

The compound represented by the formula (1-g') can be prepared by reacting the compound represented by the formula (9-b) and urea (18) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; amines such as pyridine and triethylamine; alkyl Aft ketones such as acetone, methyl ethyl ketone and methyl isobutyl ketone; alcohols such as methanol, ethanol and propanol; and water.

In this reaction, it is preferred to use urea in an amount of from 1 to 2 mole equivalents per mole of the compound of the formula (9-b). The reaction temperature may range from 0° C. to the boiling point of the solvent or so. The reaction time may range from 0.5 to 48 hours, preferably from 1 to 24 hours.

The compounds represented by the formula (2), which are raw materials for the above-described Process A, Process B, Process D, Process E, Process F and Process J, can be prepared from various compounds as raw materials, for example, in accordance with Process N or Process O which will be described below. On the other hand, 6-chloromethylthymine can be prepared by the process disclosed in literature [Journal of the American Chemical Society, 35, 596 (1913)].

[Process N]

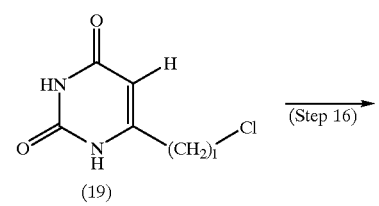

(19) (Step 16) →

-continued

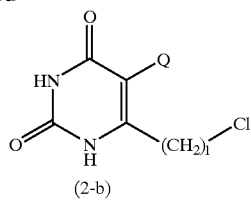

(2-b)

wherein Q represents a chlorine, bromine or iodine atom, and l stands for 1 or 2.
(Step 16)
The compound represented by the formula (2-b) can be prepared following Step 9 of Process H, using as a raw material 6-chloromethyluracil, a commercially-available compound, or 6-(2-chloroethyl)uracil, a compound already known from Journal of Heterocyclic Chemistry, 16, 239 (1979).

[Process O]

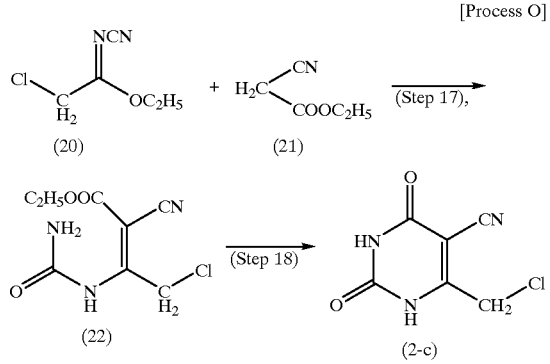

More specifically, the step shown in the above reaction formula can be practiced as will be described hereinafter.
(Step 17)
The compound (22) can be prepared by reacting ethyl 2-chloro-N-cyanoacetoimidate (20) disclosed in literature [Journal of Organic Chemistry, 28, 1816 (1963)] and ethyl cyanoacetate (21) in a suitable solvent in the presence of a basic compound in accordance with the process disclosed in literature [Journal of the Chemical Society Chemical Communications, 350 (1974)].

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as tetrahydrofuran and dioxane; alcohols such as methanol, ethanol and propanol; and water.

Illustrative basic compounds include inorganic basic compounds, e.g., alkali metal carbonates such as sodium carbonate and potassium carbonate, alkali metal bicarbonates such as sodium bicarbonate and potassium bicarbonate, alkali metal hydroxides such as sodium hydroxide and potassium hydroxide, alkali metals such as sodium and potassium, alkali metal alkoxides such as sodium methoxide, sodium ethoxide and potassium t-butoxide, and alkali metal hydrides such as sodium hydride.

In this reaction, it is preferred to use ethyl cyanoacetate (21) in an amount of from 1 to 2 mole equivalents per mole of ethyl 2-chloro-N-cyanoacetoimidate (20). The reaction temperature may range from 0° C. to the boiling point of the solvent or so, preferably from 0° C. to 80° C. The reaction time may range from 0.5 to 48 hours, preferably from 1 to 24 hours.

The compound of the formula (22) available by the above reaction can be used in Step 18 with or without isolation.
(Step 18)
The compound (2-c) can be prepared by reacting the compound (22) with sodium hydroxide in water in accordance with the process disclosed in literature [Journal of the Chemical Society Chemical Communications, 350 (1974)].

In the above reaction, it is preferred to use sodium hydroxide in an amount of from 1 to 100 mole equivalents per mole of the compound (22). The reaction temperature may range from 0° C. to the boiling point of the solvent or so, preferably from 0° C. to 50° C. The reaction time may range from 0.5 to 24 hours, preferably from 1 to 6 hours.

Further, the compound according to the present invention represented by the formula (12), which is the raw material for Process H, can be prepared, for example, by the below-described Process P, using various compounds as raw materials.

[Process P]

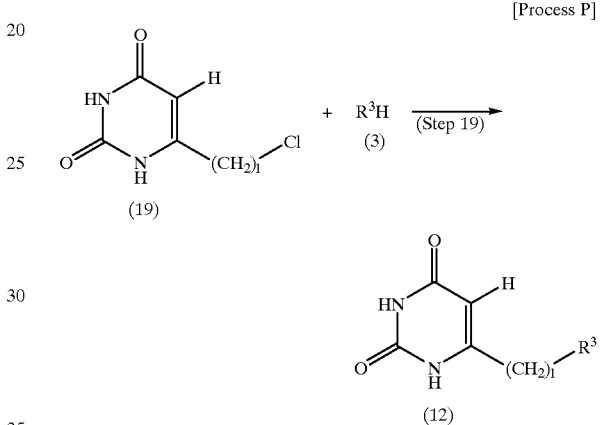

wherein $R^3$ and l have the same meanings as defined above.
(Step 19)
The compound represented by the formula (12) can be prepared following Step 1 of Process A, using 6-chloromethyluracil or 6-(2-chloroethyl)uracil (19).

The compounds (1), which have been obtained by Process A, Process B. Process C, Process D, Process E, Process F, Process G, Process H, Process I, Process J, Process K, Process L and Process M, can be used after isolating and purifying them by conventional separation means, for example, column chromatography, recrystallization, vacuum distillation or the like.

The uracil derivative (1) or its salt according to the present invention, which has been obtained as described above, has excellent human thymidine phosphorylase inhibiting effects and is useful as an effective ingredient for an antitumor effect potentiator or an antitumor agent.

The uracil derivative represented by the formula (1) or its salt is useful as an antitumor effect potentiator for an antitumor agent containing a 2'-deoxypyrimidine nucleoside. Here, illustrative of the 2'-deoxypyrimidine nucleoside are 5-trifluoromethyl-2'-deoxyuridine, thymidine, 5-fluoro-2'-deoxyuridine, prodrug derivatives [for example, PCT International Publication No. WO95/18138] of 5'-fluoro-2'-deoxyuridine, and 5-aza-2'-deoxycytidine. Of these, particularly preferred are 5-trifluoromethyl-2'-deoxyuridine and 5-fluoro-2'-deoxyuridine.

To use as an antitumor effect potentiator, the uracil derivative or its salt (1) formulated into one of dosage unit forms and an antitumor agent also formulated by itself into one of various dosage unit forms and containing a 2'-deoxypyrimidine nucleoside can be administered separately or at the same time.

As an alternative, the uracil derivative (1) or its salt can also be administered as an antitumor agent containing same and a 2'-deoxypyrimidine nucleoside after formulating it into one of various dosage unit forms. In this case, no particular limitation is imposed on the proportions of the 2'-deoxypyrimidine nucleoside and the uracil derivative (1) or its salt. It is however preferred to use the latter in an amount of from 0.1 to 500 moles or so, especially from 0.2 to 10 moles or so per mole of the former.

Upon using the antitumor effect potentiator and antitumor agent according to the present invention as therapeutics for malignant tumors of mammals including human, they can be formulated into various pharmacological dosage forms depending on the purposes of treatments. Specifically, they can be formulated into oral preparations such as tablets, coated tablets, pills, powders, granules, capsules, solutions, suspensions and emulsions; and parenteral preparations such as injections, suppositories, ointments and plasters. These dosable preparations can each be formulated by a commonly formulation method generally known in the present field of art while using a pharmaceutically acceptable carrier or the like.

Upon formulation into the form of tablets, usable examples of carriers include excipients such as lactose, sucrose, sodium chloride, glucose, urea, starch, calcium carbonate, kaolin, crystalline cellulose and silicic acid; binders such as water, ethanol, propanol, corn starch, simple syrup, glucose solution, starch solution, gelatin solution, carboxymethyl cellulose, shellac, methyl cellulose, hydroxypropyl cellulose, hydroxypropylmethyl cellulose, potassium phosphate and polyvinyl pyrrolidone; disintegrators such as dried starch, sodium alginate, powdered agar, powdered laminarin, sodium bicarbonate, calcium carbonate, polyoxyethylene sorbitan fatty acid esters, sodium lauryl sulfate, stearic acid monoglyceride, starch and lactose; disintegration suppressors such as sucrose, stearic acid, cacao butter and hydrogenated oils; absorbefacients such as quaternary ammonium bases and sodium lauryl sulfate; humectants such as glycerin and starch; adsorbents such as starch, lactose, kaolin, bentonite and colloidal silicic acid; and lubricants such as purified talc, stearate salts, powdered boric acid and polyethylene glycol. Further, tablets may be formed into those applied with conventional coatings as needed, for example, sugar-coated tablets, gelatin-coated tablets, enteric-coated tablets, film-coated tablets, double-layer tablets and multi-layer tablets.

Examples of carriers usable upon formulation into the form of pills include excipients such as glucose, lactose, starch, cacao butter, hydrogenated vegetable oils, kaolin and talc; binders such as powdered gum arabic, powdered tragacanth, gelatin and ethanol; and disintegrators such as laminarin and agar.

Capsules can be formulated by mixing the uracil derivative (1) or its salt with one or more of the above-exemplified various carriers and then filling the resultant mixture in hard gelatin capsules, soft capsules or the like.

To formulate liquid preparations for oral administration, liquid preparation for internal use, syrups and elixirs can be formulated by methods known per se in the art, using taste corrigents, buffers, stabilizers and smell corrigents. Illustrative of the taste corrigents are sucrose, bitter orange peel, citric acid and tartaric acid, illustrative of the buffers is sodium citrate, and illustrative of the stabilizers are tragacanth gum, gum arabic and gelatin.

As a carrier upon formulation into the form of suppositories, it is possible to use, for example, polyethylene glycol, cacao butter, a higher alcohol, an ester of a higher alcohol, gelatin, semisynthetic glyceride or the like.

To formulate injections, it is preferred to sterilize solutions, emulsions or suspensions and to make them isotonic with blood. Usable examples of diluents upon formulation into the form of these injections include water, an aqueous lactic acid solution, ethyl alcohol, propylene glycol, Macrogol, ethoxylated isostearyl alcohol, polyoxylated isostearyl alcohol and polyoxyethylene sorbitan fatty acid esters. In this case, such pharmaceutical preparations may contain sodium chloride, glucose or glycerin in an amount sufficient to prepare isotonic solutions. Further, conventional solubilizing aids, buffers, soothing agents, and the like may also be added.

Examples of diluents usable upon formulation into the form of ointments, for example, pastes, creams and gels include white petrolatum, paraffin, glycerin, cellulose derivatives, polyethylene glycol, silicone and bentonite.

For the formulation of a plaster, it is only necessary to coat a conventional backing material with the above-described ointment, cream, gel, paste or the like. Suitable examples of the backing material include woven fabrics or nonwoven fabrics of cotton, rayon or chemical fibers, and films or foamed sheets of soft PVC, polyethylene or polyurethane.

To the above-described preparations, a coloring matter, a preservative, a perfume, a corrigent, a sweetening and/or the like as well as another pharmaceutical can also be added as needed.

No particular limitations are imposed on the amounts of the 2'-deoxypyrimidine nucleoside and the uracil derivative (1) or the salt thereof, which are contained in each preparation according to the present invention. In general, however, it is preferred to control the content of each of them at about 1 to 70 wt. % in each preparation.

No particular limitation is imposed on the administration method for the each preparation according to the present invention. An administration method is determined as desired depending on the form of the preparation, the age, sex and other conditions of the patient, the severity of a symptom of the patient, and the like. For example, oral administration is used for tablets, pills, powders, granules capsules, solutions, suspensions and emulsions. Injections are intravenously administered either by themselves or as mixtures with a usual fluid replacement such as glucose or amino acids, and if necessary, are also administered by themselves intra-arterially, intramuscularly, intracutaneously, subcutaneously or intraperitoneally. Suppositories are administered intrarectally. Ointments are coated on the skin, the oral mucosa or the like, whereas plasters are applied on the skin.

The dose of the active ingredient in each preparation according to the present invention can be suitably chosen depending on the administration method, the age, sex and other conditions of the patient, the severity of the disease, and the like. As a general standard, the dose of the 2'-deoxypyrimidine nucleoside may range from about 0.1 to 100 mg/kg/day, preferably from about 0.5 to 50 mg/kg/day, and the dose of the uracil derivative (1) or the salt thereof may range from about 0.01 to 10000 mg/kg/day, preferably from about 0.5 to 1000 mg/kg/day. These preparations according to the present invention can each be administered once a day or in about 2 to 4 portions in a day.

Malignant tumors curable by the administration of preparations according to the present invention are not limited to any particular ones but include, for example, esophageal carcinoma, gastric cancer, liver cancer, gallbladder and bile duct cancers, pancreas cancer, colon cancer, rectum cancer, head and neck cancers, lung cancer, breast cancer, cervical cancer, ovarian cancer, bladder cancer, prostatic cancer, testis tumor, osteochondroma, skin cancer, malignant lymphoma, leukemia, brain tumor and the like.

EXAMPLES

The present invention will hereinafter be described more specifically by the following Referential Examples and Examples but shall not be limited thereto.

[Synthesis of the Compound (2-b) by Process N]

Referential Example 1

Synthesis of 5-chloro-6-chloromethyluracil

To a suspension of 6-chloromethyluracil (163 g) in acetic acid (500 ml), sulfuryl chloride (120 ml) was added dropwise at room temperature over 20 minutes, followed by stirring at the same temperature for 3 hours. The reaction mixture was poured into ice water (500 ml), and a crystallized matter was collected by filtration, whereby 182.3 g of the title compound were obtained (yield: 92%).

Melting point: 225° C. min. (decomposed).

NMR spectrum (DMSO-$d_6$) δ: 4.46(2H,s), 11.57(1H,s), 11.71(1H,s).

| Elemental analysis (as $C_5H_4N_2O_2Cl_2$): | | | |
|---|---|---|---|
| | C | H | N |
| Calculated: | 30.80 | 2.07 | 14.37 |
| Found: | 30.85 | 1.99 | 14.41 |

Referential Example 2

Synthesis of 5-bromo-6-chloromethyluracil

A reaction was conducted in a similar manner as Referential Example 1 except that N-bromosuccinimide was used instead of sulfuryl chloride, whereby the title compound was obtained in a yield of 70%.

Melting point: 245° C. min. (decomposed).

NMR spectrum (DMSO-$d_6$) δ: 4.47(2H,s), 11.61(1H,s), 11.66(1H,s).

| Elemental analysis (as $C_5H_4N_2O_2BrCl$): | | | |
|---|---|---|---|
| | C | H | N |
| Calculated: | 25.08 | 1.68 | 11.70 |
| Found: | 24.81 | 1.67 | 11.57 |

Referential Example 3

Synthesis of 5-iodo-6-chloromethyluracil

A reaction was conducted in a similar manner as Referential Example 1 except that N-iodosuccinimide was used instead of sulfuryl chloride, whereby the title compound was obtained in a yield of 77%.

Melting point: 225° C. min. (decomposed).

NMR spectrum (DMSO-$d_6$) δ: 4.49(2H,s), 11.52(1H,s), 11.58(1H,s).

| Elemental analysis (as $C_5H_4N_2O_2ClI$): | | | |
|---|---|---|---|
| | C | H | N |
| Calculated: | 20.96 | 1.41 | 9.78 |
| Found: | 21.10 | 1.36 | 9.87 |

Referential Example 4

Synthesis of 5-chloro-6-(2-chloroethyl)uracil

A reaction was conducted in a similar manner as Referential Example 1 except that 6-(2-chloroethyl)uracil was used instead of 6-chloromethyluracil, whereby the title compound was obtained in a yield of 77%.

Melting point: 225° C. min. (decomposed).

NMR spectrum (DMSO-$d_6$) δ: 3.01(2H,t,J=6.9 Hz), 3.88 (2H,t,J=6.9 Hz), 11.28(1H,s), 11.60(1H,s).

| Elemental analysis (as $C_6H_6N_2O_2Cl_2 \cdot 2/5H_2O$): | | | |
|---|---|---|---|
| | C | H | N |
| Calculated: | 33.89 | 3.03 | 13.18 |
| Found: | 34.27 | 3.02 | 12.75 |

[Synthesis of the Compound (2-c) by Process O]

Referential Example 5

Synthesis of ethyl 4-chloro-2-cyano-3-ureidocrotonate (22)

A solution of 20 g of ethyl 2-chloro-N-cyanoacetoimidate (20), 16.6 g of ethyl cyanoacetate (21) and 9.28 g of sodium ethoxide in ethanol (350 ml) was stirred at room temperature for 3 hours. After the reaction mixture was distilled, 140 ml of 2 N hydrochloric acid were added, followed by stirring under ice cooling for 1 hour. After the reaction mixture was neutralized with a 2 N aqueous solution of sodium hydroxide, the resultant mixture was extracted with ethyl acetate. The extract was washed with water, dried over anhydrous magnesium sulfate, and then concentrated under reduced pressure. The residue so obtained was purified by chromatography on a silica gel column while using gradient elution with hexane-ethyl acetate, whereby 5.66 g of the title compound were obtained (yield: 18%).

Melting point: 175–177° C.

NMR spectrum (DMSO-$d_6$) δ: 1.27(3H,t,J=6.9 Hz), 4.26 (2H,q,J=6.9 Hz), 5.38(2H,s), 10.05(1H,s).

| Elemental analysis (as $C_8H_{10}N_3O_3Cl$): | | | |
|---|---|---|---|
| | C | H | N |
| Calculated: | 41.48 | 4.35 | 18.14 |
| Found: | 41.87 | 4.44 | 17.78 |

Referential Example 6

Synthesis of 5-cyano-6-chloromethyluracil (2-b)

Dissolved in 17 ml of a 2 N aqueous solution of sodium hydroxide were 3.88 g of the ethyl 4-chloro-2-cyano-ureidocrotonate (22) obtained in Referential Example 5. The resulting mixture was stirred at room temperature for 1 hour and under ice cooling, was neutralized with 2 N hydrochloric acid. A crystallized matter was collected by filtration, whereby 1.16.g of the title compound were obtained (yield: 37%).

Melting point: 229° C. min. (decomposed).

NMR spectrum (DMSO-$d_6$) δ: 4.45(2H,s), 10.05 (1H,s).

| Elemental analysis (as $C_6H_4N_3O_2Cl.1/10H_2O$): | | | |
|---|---|---|---|
| | C | H | N |
| Calculated: | 38.46 | 2.26 | 22.43 |
| Found: | 38.72 | 2.20 | 22.07 |

[Synthesis of the Compound (12) by Process P]

Referential Example 7

Synthesis of 6-(1-pyrrolidinylmethyl)uracil

To a solution of 1.78 g of pyrrolidine in water (20 ml), 1.33 g of 6-chloromethyluracil were added. The resulting mixture was stirred at room temperature for 24 hours and neutralized with acetic acid. The reaction mixture was then concentrated under reduced pressure. The residue so obtained was washed with methanol and then filtered, whereby 466 mg of the title compound were obtained (yield: 29%).

Melting point: 176–178° C. min.

NMR spectrum (DMSO-$d_6$) δ: 1.68–1.76(4H,m), 2.42–2.55(4H,m), 3.49(2H,s), 5.44(1H,s), 10.90(2H,br-s).

| Elemental analysis (as $C_9H_{13}N_3O_2.4/5H_2O$): | | | |
|---|---|---|---|
| | C | H | N |
| Calculated: | 51.57 | 7.02 | 20.04 |
| Found: | 51.59 | 6.94 | 19.73 |

Physical properties of compounds obtained in the following Examples are presented in Table 1 to Table 20.

[Synthesis of the compound (1-a) by Process A]

Example 1

Synthesis of 5-chloro-6-(1-pyrrolidinylmethyl)uracil (Compound 1)

To a solution of 32.8 g of pyrrolidine in water (300 ml), 30.0 g of the 5-chloro-6-chloromethyluracil obtained in Referential Example 1 were added. After the resultant mixture was stirred at room temperature for 24 hours, an insoluble matter was removed by filtration. The filtrate was concentrated under reduced pressure. The residue so obtained was washed with methanol and collected by filtration, whereby 14.2 g of the title compound were obtained (yield: 40%).

Example 2

Syntheses of Compounds 2 to 21

Compounds 2 to 21, which are shown in Table 1 to Table 3 and Table 11 to Table 13, were synthesized in a similar manner as Example 1 by using appropriate starting raw materials.

Example 3

Synthesis of 5-chloro-6-(1-(3-methanesulfonyloxy) pyrrolidinylmethyl)uracil (Compound 22)

To a solution of 702 mg of the 5-chloro-6-(1-(3-hydroxy) pyrrolidinylmethyl)uracil (Compound 8), which had been obtained in Example 2, in pyridine (5 ml), 350 mg of methanesulfonyl chloride were added. After the resultant mixture was stirred at room temperature for 24 hours, the reaction mixture was purified by chromatography on a silica gel column (chloroformmethanol elution), whereby 220 mg of the title compound were obtained (yield: 24%).

Example 4

Synthesis of 5-chloro-6-(3-nitro-1,2,4-triazol-1-ylmethyl) uracil (Compound 23)

To a solution of 0.88 g of 3-nitro-1,2,4-triazole in a 1 N aqueous solution of KOH (10 ml), 0.50 g of 5-chloro-6-chloromethyluracil was added, followed by heating at 80° C. for 2.5 hours under stirring. The reaction mixture was neutralized with 6 N hydrochloric acid. A precipitate was collected by filtration and then washed with water and methanol, whereby 510 mg of the title compound were obtained (yield: 73%).

Example 5

Syntheses of Compounds 24 to 28

Compounds 24 to 28, which are shown in Table 3 to Table 4 and Table 13 to Table 14, were synthesized in a similar manner as Example 4 by using appropriate starting raw materials.

Example 6

Synthesis of 5-chloro-6-(1-(2-iminopyrrolidinyl)methyl) uracil hydrochloride (Compound 29)

A solution of 5.0 g of 5-chloro-6-chloromethyluracil, 6.14 g of 2-iminopyrrolidine and 5.24 g of sodium ethoxide in N,N-dimethylformamide (50 ml) was stirred at room temperature for 14 hours. A crystallized matter was collected by filtration and then suspended in 30 ml of water. After the suspension was neutralized with acetic acid and then washed, an insoluble matter was collected by filtration and then dissolved in 60 ml of 1 N hydrochloric acid. Activated carbon was added to the resultant solution, followed by filtration. The filtrate was concentrated under reduced pressure, and the residue so obtained was washed with ethanol and collected with filtration, whereby 2.68 g of the title compound were obtained (yield: 38%).

Example 7

Synthesis of 5-chloro-6-(1-(2-iminopyrrolidinyl)methyl) uracil p-toluenesulfonate (Compound 30)

A reaction was conducted in a similar manner as Example 6 except that p-toluenesulfonic acid was used instead of 1 N hydrochloric acid, whereby the title compound was obtained in a yield of 26%.

Example 8

Syntheses of Compounds 31 to 36

Compounds 31 to 36, which are shown in Table 4 to Table 5 and Table 14 to Table 15, were synthesized in a similar manner as Example 6 by using appropriate starting raw materials.

Example 9

Synthesis of 6-N-(2-aminoethyl)aminomethyl-5-chlorouracil (Compound 37)

To a solution of 60 g of anhydrous ethylenediamine in water (200 ml), 39 g of the 5-chloro-6-chloromethyluracil obtained in Referential Example 1 were added. The resulting mixture was stirred at room temperature for 24 hours. A crystallized matter was collected by filtration, whereby 28.35 g of the title compound were obtained (yield: 65%).

Example 10

Synthesis of 6-N-(2-aminoethyl)aminomethyl-5-bromouracil (Compound 38)

A reaction was conducted in a similar manner as Example 9 except that 5-bromo-6-chloromethyluracil was used instead of 5-chloro-6-chloromethyluracil, whereby the title compound was obtained in a yield of 46%.

Example 11

Synthesis of 6-N-(2-aminoethyl)aminomethyl-5-iodouracil (Compound 39)

A reaction was conducted in a similar manner as Example 9 except that 5-iodo-6-chloromethyluracil was used instead of 5-chloro-6-chloromethyluracil, whereby the title compound was obtained in a yield of 69%.

Example 12

Syntheses of Compounds 40 to 43

Compounds 40 to 43, which are shown in Table 5 to Table 6 and Table 15, were synthesized in a similar manner as Example 9 by using appropriate starting raw materials.

Example 13

Synthesis of 5-chloro-6-(3-hydroxypropylamino)uracil (Compound 44)

To a solution of 580 mg of 3-hydroxypropylamine in water (20 ml), 500 mg of the 5-chloro-6-chloromethyluracil obtained in Referential Example 1 were added, followed by stirring at room temperature for 19 hours. The reaction mixture was concentrated under reduced pressure and a crude product so obtained was purified by chromatography on a silica gel column (chloroform-methanol-triethylamine elution), whereby 70 mg of the title compound were obtained (yield: 12%).

Example 14

Syntheses of Compounds 45 and 46

Compounds 45 and 46, which are shown in Table 6 and Table 16, were synthesized in a similar manner as Example 13 by using appropriate starting raw materials.
[Synthesis of Compound (1-a') by Process B]

Example 15

Synthesis of 5-chloro-6-(1-(2-iminoimidazolidinyl)methyl)uracil (Compound 47)

To a solution of 3.6 g of cyanogen bromide in water (50 ml), 7.0 g of 6-N-(2-aminoethyl)aminomethyl-5-chlorouracil obtained in Example 9 were added, followed by stirring at room temperature for 3.5 hours. A crystallized matter was collected by filtration, washed with N,N-dimethylformamide and then suspended in 50 ml of water. The suspension was neutralized with a 1 N aqueous solution of sodium hydroxide and an insoluble matter was collected, whereby 2.65 g of the title compound were obtained (yield: 34%).

Example 16

Syntheses of Compounds 48 and 49

Compounds 48 and 49, which are shown in Table 6 and Table 16, were synthesized in a similar manner as Example 15 by using appropriate starting raw materials.
[Synthesis of Compound (1-b) by Process C]

Example 17

Synthesis of 5-chloro-6-(2-imidazolin-1-ylmethyl)uracil hydrochloride (Compound 50)

To a solution of 1.0 g of the 6-N-(2-aminoethyl)aminomethyl-5-chlorouracil, which had been obtained in Example 9, in acetic acid (3 ml), 0.56 ml of triethyl orthoformate was added, followed by heating for 1 hour under reflux. To the reaction mixture, 0.1 ml of concentrated hydrochloric acid and 2 ml of acetic acid were added. The resultant mixture was then allowed to cool down. A crystallized matter was collected by filtration and then washed with N,N-dimethylformamide, whereby 220 mg of the title compound were obtained (yield: 18%).
[Synthesis of Compound (1-b') by Process D]

Example 18

Synthesis of 5-chloro-6-(1-imidazolylmethyl)uracil hydrochloride (Compound 51)

To a solution of 4.3 g of N-acetylimidazole in methanol (100 ml), 5.0 g of 5-chloro-6-chloromethyluracil were added, followed by heating for 2 days under reflux. After the reaction mixture was allowed to cool down, a crystallized matter was collected by filtration and then washed with a 10% solution of hydrochloric acid in methanol, whereby 4.32 g of the title compound were obtained (yield: 64%).

Example 19

Synthesis of 5-chloro-6-(1,2,3-triazol-1-ylmethyl)uracil (Compound 52)

A reaction was conducted in a similar manner as Example 18 except that N-acetyl-1,2,3-triazole was used instead of N-acetylimidazole, whereby the title compound was obtained in a yield of 58%.
[Synthesis of Compound (1-c) by Process E]

Example 20

Synthesis of 2-(5-chlorouracil-6-ylmethyl)isothiourea hydrochloride (Compound 53)

To a solution of 140 mg of thiourea in ethanol (3 ml), 300 mg of 5-chloro-6-chloromethyluracil were added, followed by heating for 6 hours under reflux. After the reaction mixture was allowed to cool down, a crystallized matter was collected by filtration, whereby 337 mg of the title compound were obtained (yield: 81%).

Example 21

Syntheses of Compounds 54 to 58

Compounds 54 to 58, which are shown in Table 7 and Table 17, were synthesized in a similar manner as Example 20 by using appropriate starting raw materials.
[Synthesis of Compound (9) by Process F]

Example 22

Synthesis of 6-aminomethyl-5-chlorouracil (Compound 59)

To 400 ml of a 25% aqueous solution of ammonia, 10 g of the 5-chloro-6-chloromethyluracil obtained in Referential Example 1 were added, followed by stirring at room temperature for 4 days. A crystallized matter was collected by filtration, whereby 7.3 g of the title compound were obtained (yield: 81%).

Example 23

Synthesis of 5-chloro-6-N-methylaminomethyluracil (Compound 60)

To 150 ml of a 40% aqueous solution of methylamine, 6 g of the 5-chloro-6-chloromethyluracil obtained in Referential Example 1 were added. The resulting mixture was stirred at room temperature for 4.5 hours and then concentrated under reduced pressure. The residue so obtained was washed with methanol and then collected by filtration, whereby 5.38 g of the title compound were obtained (yield: 92%).

Example 24

Syntheses of Compounds 61 to 67

Compounds 61 to 67, which are shown in Table 8 and Table 17 to Table 18, were synthesized in a similar manner as Example 23 by using appropriate starting raw materials.

[Synthesis of Compound (1-d) by Process F]

Example 25

Synthesis of 5-chloro-6-(1-guanidino)methyluracil hydrochloride (Compound 68)

Subsequent to addition of 455 mg of 2-methylisothiourea sulfate to 33 ml of a 0.1 N aqueous solution of potassium hydroxide under ice cooling, 600 mg of the 6-aminomethyl-5-chlorouracil obtained in Example 22 were added, followed by heating for 2 hours at 80° C. under stirring. After the reaction mixture was allowed to cool down, a crystallized matter was collected by filtration and washed with 2 N hydrochloric acid, whereby 287 mg of the title compound were obtained (yield: 33%).

Example 26

Syntheses of Compounds 69 to 72

Compounds 69 to 72, which are shown in Table 9 and Table 18, were synthesized in a similar manner as Example 25 by using appropriate starting raw materials.

[Synthesis of Compound (1-e) by Process G]

Example 27

Synthesis of N-(5-chlorouracil-6-ylmethyl)acetamidine hydrochloride (Compound 73)

To a solution of 705 mg of ethyl acetoimidate hydrochloride in N,N-dimethylformamide (12 ml), 500 mg of 6-aminomethyl-5-chlorouracil were added, followed by stirring at room temperature for 13 hours. After the reaction mixture was allowed to cool down, a crystallized matter was collected by filtration and then washed with a 10% solution of hydrochloric acid in methanol, whereby 190 mg of the title compound were obtained (yield: 26%).

[Synthesis of Compound (1-a″) by Process H]

Example 28

Synthesis of 5-bromo-6-(1-pyrrolidinylmethyl)uracil (Compound 2)

To a solution of 1.0 g of the 6-(1-pyrrolidinylmethyl) uracil, which had been obtained in Referential Example 7, in acetic acid (10 ml), 1.0 g of bromine was added dropwise, followed by stirring at room temperature for 20 hours. A crystallized matter was collected by filtration and then washed with methanol, whereby 560 mg of the title compound were obtained (yield: 40%). The melting point and NMR spectrum of the thus-obtained compound were in full conformity with those of Compound 2 synthesized by Process A in Example 2.

| Elemental analysis (as $C_9H_{12}N_3O_2Br$): | | | |
|---|---|---|---|
|  | C | H | N |
| Calculated: | 39.44 | 4.41 | 15.33 |
| Found: | 39.48 | 4.47 | 15.43 |

[Synthesis of Compound (1-b‴) by Process I]

Example 29

Synthesis of 5-chloro-(1-pyrrolylmethyl)uracil (Compound 74)

To a solution of 500 mg of the 6-aminomethyl-5-chlorouracil, which had been obtained in Example 22, in acetic acid (8 ml), 577 mg of 2,5-dimethoxytetrahydrofuran were added, followed by heating at 110° C. for 2 hours under stirring. The temperature of the reaction mixture was cooled back to room temperature. After an insoluble matter was filtered off, the filtrate was concentrated under reduced pressure. The residue so obtained was purified by chromatography on a silica gel column (chloroform-methanol elution), whereby 155 mg of the title compound were obtained (yield: 24%).

[Synthesis of Compound (1-f) by Process J]

Example 30

Synthesis of 5-chloro-6-(2-imidazolylthiomethyl)uracil (Compound 75)

A reaction was conducted in a similar manner as Example 20 except that 2-mercaptoimidazole was used instead of thiourea, whereby the title compound was obtained in a yield of 77%.

Example 31

Syntheses of Compounds 76 to 80

Compounds 76 to 80, which are shown in Table 9 to Table 10 and Table 19, were synthesized in a similar manner as Example 30 by using appropriate starting raw materials.

[Synthesis of Compound (1-g) by Process K]

Example 32

Synthesis of N-methyl-N'-(5-chlorouracil-6-ylmethyl) thiourea (Compound 81)

A suspension of 0.50 g of 5-chloro-6-chloromethyluracil and 0.22 g of methyl isothiocyanate in N,N-dimethylformamide (3 ml) was heated at 70° C. for 4 hours under stirring. Water (50 ml) was added to the reaction mixture. A crystallized matter was collected by filtration and then washed with water and methanol, whereby 435 mg of the title compound were obtained (yield: 61%).

[Synthesis of Compound (1-d') by Process L]

Example 33

Synthesis of N-cyano-N'-methyl-N"(5-chlorouracil-6-ylmethyl)guanidine (Compound 82)

A suspension of 1.0 g of the 6-aminomethyl-5-chlorouracil obtained in Example 22 and 0.926 g of S,S'-dimethyl-N-cyanodithioiminocarbonate in N,N-dimethylformamide (20 ml) was heated at 120° C. for 3.5 hours under stirring. The reaction mixture was concentrated under reduced pressure. Methanol was added to the residue, followed by filtration. The filtrate was concentrated under reduced pressure. The residue was purified by chromatography on a silica gel column (chloroform-methanol elution), whereby 190 mg of N-cyano-N'-(5-chlorouracil-6-ylmethyl)-S-methylisothiourea were obtained.

Next, 150 mg of the N-cyano-N'-(5-chlorouracil-6-ylmethyl)-S-methylisothiourea were suspended in ethanol (3 ml), followed by the addition of 2 ml of a 30% solution of methylamine in ethanol. The resulting mixture was heated at 50° C. for 3.5 hours under stirring. After an insoluble matter was filtered off, the filtrate was allowed to cool back to room temperature. A precipitate from the filtrate was collected by filtration, whereby 12 mg of the title compound were obtained (yield: 96%).

[Synthesis of Compound (1-g') by Process M]

Example 34

Synthesis of 5-chloro-6-(ureidomethyl)uracil (Compound 83)

6-Aminomethyl-5-chlorouracil (300 mg) obtained in Example 22 was suspended in 2 N hydrochloric acid (10 ml), followed by concentration under reduced pressure. To the residue, 188 mg of urea and 15 ml of water were added, followed by heating for 24 hours under reflux. After an insoluble matter was filtered off, the filtrate was allowed to cool back to room temperature. A precipitate was collected by filtration and then recrystallized from water, whereby 33 mg of the title compound were obtained (yield: 9%).

TABLE 1

| Comp'd No. | $R^1$ | $R^2$ | m.p. (° C.) Molecular formula | Yield (%) | Elemental analysis (%) Calculated (Found) | | |
|---|---|---|---|---|---|---|---|
| | | | | | C | H | N |
| 1 | Cl | —N(piperidine) | 207–209 $C_9H_{12}N_3O_2Cl$ | 40 | 47.07 (46.97 | 5.27 5.36 | 18.30 18.15) |
| 2 | Br | —N(piperidine) | 213–215 $C_9H_{12}N_3O_2Br$ | 60 | 39.44 (39.54 | 4.41 4.44 | 15.33 15.49) |
| 3 | I | —N(piperidine) | 178 min. (decomp) $C_9H_{12}N_3O_2I$ | 17 | 33.66 (33.73 | 3.77 3.89 | 13.09 13.05) |
| 4 | CN | —N(piperidine) | 205 min. (decomp) $C_{10}H_{12}N_4O_2 \cdot H_2O$ | 17 | 50.41 (50.70 | 5.92 5.57 | 23.52 23.29) |
| 5 | $CH_3$ | —N(piperidine) | 196–198 $C_{10}H_{15}N_3O_2 \cdot 1/5H_2O$ | 25 | 56.43 (56.39 | 7.29 7.36 | 19.74 19.62) |
| 6 | Cl | —N(azetidine) | 190–191 $C_8H_{10}N_3O_2Cl$ | 40 | 44.56 (44.34 | 4.67 4.72 | 19.49 19.35) |

TABLE 1-continued

[Structure: pyrimidine-2,4-dione with R1 at 5-position and CH2-R2 at 6-position]

| Comp'd No. | R¹ | R² | m.p. (° C.) Molecular formula | Yield (%) | Elemental analysis (%) Calculated (Found) | | |
|---|---|---|---|---|---|---|---|
| | | | | | C | H | N |
| 7 | Cl | [1-methyl-3,5-dimethylpiperidinyl] | 220 min. (decomp) $C_{11}H_{16}N_3O_2Cl$ | 9 | 51.27 (51.13 | 6.26 6.41 | 16.30 16.34) |
| 8 | Cl | [1-methyl-3-hydroxypiperidinyl] | 190 min. (decomp) $C_9H_{12}N_3O_3Cl$ | 22 | 44.00 (44.06 | 4.92 5.08 | 17.10 16.94) |

TABLE 2

[Structure: pyrimidine-2,4-dione with R1 at 5-position and CH2-R2 at 6-position]

| Comp'd No. | R¹ | R² | m.p. (° C.) Molecular formula | Yield (%) | Elemental analysis (%) Calculated (Found) | | |
|---|---|---|---|---|---|---|---|
| | | | | | C | H | N |
| 9 | Cl | [(R)-1-methyl-3-(hydroxymethyl)piperidinyl] | 165–167 $C_{10}H_{14}N_3O_3Cl$ | 53 | 46.25 (46.23 | 5.43 5.60 | 16.18 15.99) |
| 10 | Cl | [(S)-1-methyl-3-(hydroxymethyl)piperidinyl] | 165–167 $C_{10}H_{14}N_3O_3Cl$ | 22 | 46.25 (46.46 | 5.43 5.65 | 16.18 16.10) |
| 11 | Cl | [1-methyl-3-aminopiperidinyl·2HCl] | 220 min. (decomp) $C_9H_{13}N_4O_2Cl$ 2HCl1/5H₂O | 91 | 33.65 (33.65 | 4.83 4.93 | 17.44 17.41) |
| 12 | Cl | [1-methyl-1,4,5,6-tetrahydropyrimidinyl] | 233–236 $C_8H_9N_4O_2Cl$ | 99 | 42.03 (41.72 | 3.97 3.86 | 24.50 24.10) |

TABLE 2-continued

[Structure: pyrimidine-2,4-dione with R₁ at 5-position and CH₂R₂ at 6-position]

| Comp'd No. | R¹ | R² | m.p. (° C.) Molecular formula | Yield (%) | Elemental analysis (%) Calculated (Found) | | |
|---|---|---|---|---|---|---|---|
| | | | | | C | H | N |
| 13 | Cl | piperidinyl | 195 min. (decomp) $C_{10}H_{14}N_3O_2Cl$ | 61 | 49.29 (49.37 | 5.79 5.83 | 17.24 17.15) |
| 14 | Br | piperidinyl | 215 min. (decomp) $C_{10}H_{14}N_3O_2Br$ | 30 | 41.68 (41.70 | 4.90 5.00 | 14.58 14.54) |
| 15 | Cl | 4-methylpiperazinyl | 205 min. (decomp) $C_{10}H_{15}N_4O_2Cl$ | 1 | 46.43 (46.44 | 5.84 6.05 | 21.66 21.53) |
| 16 | Cl | morpholinyl | 245 $C_9H_{12}N_3O_3Cl$ 1/10H₂O | 78 | 43.68 (43.68 | 4.97 4.81 | 16.98 16.89) |
| 17 | Cl | homopiperidinyl (azepanyl) | 200 min. (decomp) $C_{11}H_{16}N_3O_2Cl$ | 47 | 51.27 (51.39 | 6.26 6.50 | 16.30 16.37) |

TABLE 3

[Structure: pyrimidine-2,4-dione with R₁ at 5-position and CH₂R₂ at 6-position]

| Comp'd No. | R¹ | R² | m.p. (° C.) Molecular formula | Yield (%) | Elemental analysis (%) Calculated (Found) | | |
|---|---|---|---|---|---|---|---|
| | | | | | C | H | N |
| 18 | Cl | azocanyl | 175 min. (decomp) $C_{12}H_{18}N_3O_2Cl$ | 46 | 53.04 (53.03 | 6.68 7.03 | 15.46 15.39) |
| 19 | Cl | —CH₂—piperidinyl | 270 min. (decomp) $C_{10}H_{14}N_3O_2Cl$ | 14 | 49.29 (49.00 | 5.79 6.02 | 17.24 16.90) |

TABLE 3-continued

| Comp'd No. | R¹ | R² | m.p. (° C.) Molecular formula | Yield (%) | Elemental analysis (%) Calculated (Found) | | |
|---|---|---|---|---|---|---|---|
| | | | | | C | H | N |
| 20 | Cl | [N-methyl-N'-methyl cyclic amidine · HCl] | 250 min. (decomp) $C_9H_{10}N_5O_2Cl$ 1/4$H_2O$ | 24 | 36.44 (36.41 | 3.91 3.86 | 23.61 23.55) |
| 21 | Cl | [N-methyl-N'-ethyl cyclic amidine · HCl] | 235 min. (decomp) $C_{10}H_{12}N_5O_2Cl$ $H_2O$ | 7 | 37.05 (37.33 | 4.66 4.33 | 21.60 21.52) |
| 22 | Cl | [N-methyl piperidinyl methanesulfonate] | 175 min. (decomp) $C_{10}H_{14}N_3O_5SCl$ | 47 | 37.10 (36.93 | 4.36 4.40 | 12.98 12.80) |
| 23 | Cl | [N-methyl-2-nitroimino triazinane] | 230 min. (decomp) $C_7H_5N_6O_4Cl$ | 73 | 30.84 (30.34 | 1.85 1.76 | 30.83 31.12) |
| 24 | Cl | [N-methyl dihydropyrimidine] | 220 min. (decomp) $C_8H_7N_4O_2Cl$ | 17 | 42.40 (42.01 | 3.11 3.05 | 24.72 24.39) |

TABLE 4

| Comp'd No. | R¹ | R² | m.p. (° C.) Molecular formula | Yield (%) | Elemental analysis (%) Calculated (Found) | | |
|---|---|---|---|---|---|---|---|
| | | | | | C | H | N |
| 25 | Cl | [N-methyl-2-methyl dihydropyrazine · HCl] | 240 min. (decomp) $C_9H_9N_4O_2Cl$ HCl5/4$H_2O$ | 8 | 36.08 (36.03 | 4.20 3.94 | 18.71 18.44) |

TABLE 4-continued

[Structure: pyrimidine-2,4-dione with R₁ at 5-position and CH₂-R₂ at 6-position]

| Comp'd No. | R¹ | R² | m.p. (° C.) Molecular formula | Yield (%) | Elemental analysis (%) Calculated (Found) | | |
|---|---|---|---|---|---|---|---|
| | | | | | C | H | N |
| 26 | Cl | [1-methyl-3-nitro-pyrimidin-2(1H)-ylidene-methyl] | 185 min. (decomp) C₈H₆N₅O₄Cl | 50 | 35.38 (35.27 | 2.23 2.22 | 25.78 25.68) |
| 27 | Cl | [1-methyl-6-nitro-pyrimidin-2(1H)-ylidene-methyl] | 155–158 C₈H₆N₅O₄Cl 5/4H₂O | 12 | 32.67 (32.87 | 2.91 2.73 | 23.81 23.60) |
| 28 | Cl | [1-methyl-1,3,5-triazin-2(1H)-ylidene-methyl] | 235 min. (decomp) C₇H₆N₅O₂Cl 1/5H₂O | 14 | 36.36 (36.74 | 2.79 2.71 | 30.29 29.96) |
| 29 | Cl | [1-methyl-piperidin-2-ylidene-amine · HCl] | 255 min. (decomp) C₉H₁₁N₄O₂Cl HCl1/10H₂O | 38 | 38.48 (38.32 | 4.38 4.35 | 19.94 19.68) |
| 30 | Cl | [1-methyl-piperidin-2-ylidene-amine · TsOH] | 210 min. (decomp) C₉H₁₁N₄O₂Cl TsOH1/10H₂O | 26 | 46.12 (45.71 | 4.64 4.59 | 13.45 13.89) |
| 31 | Br | [1-methyl-piperidin-2-ylidene-amine · HCl] | 180 min. (decomp) C₉H₁₁N₄O₂Br HCl5/4H₂O | 13 | 31.23 (31.23 | 4.22 4.31 | 16.19 16.16) |
| 32 | CH₃ | [1-methyl-piperidin-2-ylidene-amine · HCl] | 250 min. (decomp) C₁₀H₁₄N₄O₂ HCl1/2H₂O | 45 | 44.86 (44.55 | 6.02 6.14 | 20.93 20.72) |

TABLE 5

$$\text{Structure: pyrimidine-2,4-dione with } R_1 \text{ at 5-position and } CH_2R_2 \text{ at 6-position}$$

| Comp'd No. | R¹ | R² | m.p. (° C.) Molecular formula | Yield (%) | Calculated (Found) C | H | N |
|---|---|---|---|---|---|---|---|
| 33 | CN | piperidin-2-imine-N-yl (6-membered ring with =NH) | 263 min. (decomp) $C_{10}H_{11}N_5O_2$ 1/4$H_2O$ | 29 | 50.52 (50.56 | 4.88 4.70 | 29.46 29.25) |
| 34 | Cl | 1-methyl-imidazolidin-2-imine type (NCH₃) | 215 min. (decomp) $C_9H_{12}N_5O_2Cl$ | 22 | 41.95 (41.64 | 4.69 4.75 | 27.18 26.80) |
| 35 | Cl | N-ethyl analog (NC₂H₅) | 205 min. (decomp) $C_{10}H_{14}N_5O_2Cl$ 1/6$H_2O$ | 11 | 43.72 (43.69 | 5.26 5.23 | 25.49 25.51) |
| 36 | Cl | N-isopropyl analog (N-CH(CH₃)₂) | 220 min. (decomp) $C_{11}H_{16}N_5O_2Cl$ 4/5$H_2O$ | 15 | 44.02 (44.07 | 5.91 5.90 | 23.33 23.37) |
| 37 | Cl | —NH(CH₂)₂NH₂ | 140 min. (decomp) $C_7H_{11}N_4O_2Cl$ 1/3$H_2O$ | 70 | 37.43 (37.44 | 5.23 5.47 | 23.33 24.94) |
| 38 | Br | —NH(CH₂)₂NH₂ | 168 min. (decomp) $C_7H_{11}N_4O_2Br$ | 46 | 31.96 (31.73 | 4.21 4.31 | 21.30 21.32) |
| 39 | I | —NH(CH₂)₂NH₂ | 145 min. (decomp) $C_7H_{11}N_4O_2I$ | 69 | 27.11 (27.01 | 3.58 3.70 | 18.07 17.91) |
| 40 | Cl | —NH—N(CH₃)₂·HCl | 160 min. (decomp) $C_7H_{12}N_4O_2Cl_2$ | 94 | 32.96 (32.83 | 4.74 4.92 | 21.96 21.93) |
| 41 | Cl | —NH(CH₂)₂N(CH₃)₂ | 160 min. (decomp) $C_9H_{15}N_4O_2Cl$ 3/2HCl3/2$H_2O$ | 23 | 32.92 (32.90 | 5.98 6.05 | 17.06 17.14) |

TABLE 6

$$\text{Structure: pyrimidine-2,4-dione with } R^1 \text{ at 5-position and } CH_2R^2 \text{ at 6-position}$$

| Comp'd No. | R¹ | R² | m.p. (° C.) Molecular formula | Yield (%) | Calculated (Found) C | H | N |
|---|---|---|---|---|---|---|---|
| 42 | Cl | —NH(CH₂)₃NH₂ | 135 min. (decomp) $C_8H_{13}N_4O_2Cl$ 1/10$H_2O$ | 6 | 40.98 (40.99 | 5.67 5.89 | 23.89 23.56) |
| 43 | Cl | —NH(CH₂)₂CN | 205 min. (decomp) $C_8H_9N_4O_2Cl$ | 89 | 42.03 (42.05 | 3.97 3.89 | 24.50 24.35) |

TABLE 6-continued

[Structure: pyrimidine-2,4-dione with $R^1$ at 5-position and $CH_2R^2$ at 6-position]

| Comp'd No. | $R^1$ | $R^2$ | m.p. (° C.) Molecular formula | Yield (%) | Calculated (Found) C | H | N |
|---|---|---|---|---|---|---|---|
| 44 | Cl | —NH(CH$_2$)$_3$OH | 167–169<br>C$_8$H$_{12}$N$_3$O$_2$Cl | 12 | 41.12<br>(41.12 | 5.18<br>5.43 | 17.98<br>18.05) |
| 45 | Cl | —N(CH$_3$)(CH$_2$)$_2$OH | 159–160<br>C$_8$H$_{12}$N$_3$O$_3$Cl | 38 | 41.12<br>(41.17 | 5.19<br>5.35 | 17.98<br>17.93) |
| 46 | Cl | —NH(CH$_2$)$_4$OH | 164–166<br>C$_9$H$_{14}$N$_3$O$_3$Cl | 2 | 43.64<br>(43.57 | 5.70<br>5.92 | 16.97<br>16.72) |
| 47 | Cl | [2-iminohexahydropyrimidin-1-yl] | 228 min. (decomp)<br>C$_8$H$_{10}$N$_5$O$_2$Cl<br>5/4H$_2$O | 34 | 36.10<br>(36.10 | 4.73<br>4.67 | 26.31<br>26.24) |
| 48 | Br | [2-iminohexahydropyrimidin-1-yl] | 235 min. (decomp)<br>C$_8$H$_{10}$N$_5$O$_2$Br<br>5/4H$_2$O | 25 | 30.93<br>(31.05 | 4.06<br>3.96 | 22.55<br>22.70) |
| 49 | I | [2-iminohexahydropyrimidin-1-yl] | 207 min. (decomp)<br>C$_8$H$_{10}$N$_5$O$_2$I<br>4/5H$_2$O | 4 | 27.49<br>(27.87 | 3.35<br>3.15 | 20.04<br>19.54) |
| 50 | Cl | [3,4,5,6-tetrahydropyrimidin-1-yl]·HCl | 260 min. (decomp)<br>C$_8$H$_9$N$_4$O$_2$Cl<br>HCl | 18 | 36.38<br>(36.34 | 3.82<br>3.83 | 21.21<br>20.87) |

TABLE 7

[Structure: pyrimidine-2,4-dione with $R^1$ at 5-position and $CH_2R^2$ at 6-position]

| Comp'd No. | $R^1$ | $R^2$ | m.p. (° C.) Molecular formula | Yield (%) | Calculated (Found) C | H | N |
|---|---|---|---|---|---|---|---|
| 51 | Cl | [pyrimidin-1-yl]·HCl | 244–246<br>C$_8$H$_7$N$_4$O$_2$Cl<br>HCl2/3H$_2$O | 64 | 34.93<br>(35.14 | 3.42<br>3.36 | 20.37<br>20.07) |

TABLE 7-continued

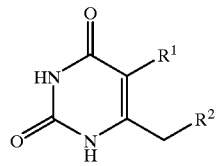

| Comp'd No. | R¹ | R² | m.p. (° C.) Molecular formula | Yield (%) | Elemental analysis (%) Calculated (Found) | | |
|---|---|---|---|---|---|---|---|
| | | | | | C | H | N |
| 52 | Cl | ![N-triazine-CH2] | 195 min. (decomp) $C_7H_6N_5O_2Cl$ 1/5$H_2O$ | 58 | 36.36 (35.98 | 2.79 2.56 | 30.29 30.63) |
| 53 | Cl | -S-C(NH₂)=NH·HCl (methylthio) | 220 min. (decomp) $C_6H_7N_4O_2ClS$ HCl | 81 | 26.58 (26.93 | 2.97 3.05 | 20.66 20.31) |
| 54 | Br | -S-C(NH₂)=NH·HCl | 235 min. (decomp) $C_6H_7N_4O_2BrS$ HCl | 23 | 22.84 (22.97 | 2.56 2.68 | 17.75 17.54) |
| 55 | CH₃ | -S-C(NH₂)=NH·HCl | 160 min. (decomp) $C_7H_{10}N_4O_2S$ HCl$H_2O$ | 23 | 31.29 (31.34 | 4.88 5.06 | 20.85 20.90) |
| 56 | CN | -S-C(NH₂)=NH·HCl | 178 min. (decomp) $C_7H_7N_5O_2S$ HCl | 59 | 32.13 (32.33 | 3.08 2.97 | 26.76 26.50) |
| 57 | Cl | -S-C(NHCH₃)=NH·HCl | 205 min. (decomp) $C_7H_9N_4O_2ClS$ HCl | 93 | 29.49 (29.61 | 3.53 3.60 | 19.65 19.70) |
| 58 | Cl | -S-C(NHCH₃)=NCH₃·HCl | 200 min. (decomp) $C_8H_{11}N_4O_2ClS$ HCl | 61 | 32.12 (32.04 | 4.04 4.15 | 18.73 18.54) |
| 59 | Cl | —NH₂ | 210 $C_5H_6N_3O_2$ 1/10$H_2O$ | 81 | 33.86 (34.28 | 3.52 3.36 | 23.69 23.20) |

TABLE 8

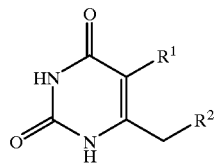

| Comp'd No. | R¹ | R² | m.p. (° C.) Molecular formula | Yield (%) | Elemental analysis (%) Calculated (Found) | | |
|---|---|---|---|---|---|---|---|
| | | | | | C | H | N |
| 60 | Cl | —NHCH₃ | 197–199 $C_6H_8N_3O_2Cl$ | 92 | 38.01 (37.62 | 4.25 4.26 | 22.16 21.94) |
| 61 | Cl | —N(CH₃)₂ | 130 min. (decomp) $C_7H_{10}N_3O_2Cl$ | 22 | 41.29 (41.25 | 4.95 5.01 | 20.64 20.42) |
| 62 | Cl | —NHC₂H₅ | 189–191 | 52 | 40.57 | 5.06 | 20.28 |

TABLE 8-continued

[Structure: pyrimidine-2,4-dione with R¹ at 5-position and CH₂R² at 6-position]

| Comp'd No. | R¹ | R² | m.p. (° C.) Molecular formula | Yield (%) | Elemental analysis (%) Calculated (Found) | | |
|---|---|---|---|---|---|---|---|
| | | | | | C | H | N |
| | | | $C_7H_{10}N_3O_2Cl$ 1/5H₂O | | (40.60 | 5.11 | 20.05) |
| 63 | Cl | —N(C₂H₅)₂ | 155 min. (decomp) $C_9H_{14}N_3O_2Cl$ | 33 | 46.66 (46.39 | 6.09 6.28 | 18.14 17.95) |
| 64 | Cl | —NH(CH₂)₂CH₃ | 193–195 $C_8H_{12}N_3O_2Cl$ 1/5H₂O | 75 | 43.43 (43.60 | 5.65 5.85 | 18.99 18.98) |
| 65 | Cl | —NHCH(CH₃)₂ | 185 min. (decomp) $C_8H_{12}N_3O_2Cl$ 1/4H₂O | 6 | 43.25 (43.31 | 5.67 5.80 | 18.91 18.86) |
| 66 | Cl | —CH₂NHCH₃ | 256 min. (decomp) $C_7H_{10}N_3O_2Cl$ 1/2H₂O | 21 | 39.54 (39.67 | 5.21 5.21 | 19.76 19.42) |
| 67 | Cl | —CH₂N(CH₃)₂ | 263 min. (decomp) $C_8H_{12}N_3O_2Cl$ | 67 | 44.15 (43.83 | 5.56 5.79 | 19.31 18.84) |
| 68 | Cl | [H-N-C(=NH·HCl)-NH₂ methyl substituted] | 255 min. (decomp) $C_6H_8N_5O_2Cl$ HCl1/10H₂O | 33 | 28.16 (28.37 | 3.62 3.67 | 27.37 27.13) |

TABLE 9

[Structure: pyrimidine-2,4-dione with R¹ at 5-position and CH₂R² at 6-position]

| Comp'd No. | R¹ | R² | m.p. (° C.) Molecular formula | Yield (%) | Elemental analysis (%) Calculated (Found) | | |
|---|---|---|---|---|---|---|---|
| | | | | | C | H | N |
| 69 | Cl | [CH₃-N-C(=NH)-NH₂] | 200 min. (decomp) $C_7H_{10}N_5O_2Cl$ H₂O | 22 | 33.68 (33.96 | 4.84 4.97 | 28.05 27.92) |
| 70 | Cl | [H-N-C(=NH·HCl)-NHCH₃] | 172 min. (decomp) $C_7H_{10}N_5O_2Cl$ HClH₂O | 42 | 29.65 (29.39 | 4.23 4.58 | 24.17 24.48) |
| 71 | Cl | [H-N-C(=NCH₃·HCl)-NHCH₃] | 189 min. (decomp) $C_8H_{12}N_5O_2Cl$ HClH₂O | 12 | 32.01 (32.37 | 5.04 5.26 | 23.33 23.14) |

TABLE 9-continued

Structure: Pyrimidine-2,4-dione with R¹ at 5-position and CH₂R² at 6-position:

$$\text{HN-C(=O)-C(R}^1\text{)=C(CH}_2\text{R}^2\text{)-NH-C(=O)}$$ (pyrimidinedione ring)

| Comp'd No. | R¹ | R² | m.p. (° C.) Molecular formula | Yield (%) | Calculated (Found) C | H | N |
|---|---|---|---|---|---|---|---|
| 72 | Cl | —NH—(2-imidazolinyl)·HCl | 235 min. (decomp) $C_8H_{10}N_5O_2Cl$ HCl1/2H₂O | 25 | 33.23 (33.26 | 4.18 4.09 | 24.22 24.13) |
| 73 | Cl | —NH—C(CH₃)=NH·HCl | 220 min. (decomp) $C_7H_9N_4O_2Cl$ HCl3/5H₂O | 26 | 31.86 (31.68 | 4.28 4.13 | 21.23 21.49 |
| 74 | Cl | N-pyridinyl | 210 min. (decomp) $C_9H_8N_3O_2Cl$ 1/5H₂O | 24 | 47.16 (47.63 | 3.69 3.70 | 18.33 17.92 |
| 75 | Cl | —S-(imidazol-2-yl)·HCl | 195 min. (decomp) $C_8H_7N_4O_2SCl$ HCl2/5C₂H₅OH | 77 | 33.71 (33.85 | 3.34 3.45 | 17.87 17.71 |
| 76 | Cl | —S-(2-imidazolinyl)·HCl | 220 min. (decomp) $C_8H_9N_4O_2SCl$ HCl | 80 | 32.34 (32.46 | 3.39 3.40 | 18.85 18.98 |

TABLE 10

Structure: Pyrimidine-2,4-dione with R¹ at 5-position and CH₂R² at 6-position.

| Comp'd No. | R¹ | R² | m.p. (° C.) Molecular formula | Yield (%) | Calculated (Found) C | H | N |
|---|---|---|---|---|---|---|---|
| 77 | Cl | —S-(1-methylimidazol-2-yl)·HCl | 210 min. (decomp) $C_9H_9N_4O_2SCl$ HCl | 87 | 34.96 (34.90 | 3.26 3.31 | 18.12 17.98 |
| 78 | Cl | —S-(1,2,4-triazol-3-yl)·HCl | 215 min. (decomp) $C_7H_6N_5O_2SCl$ HCl | 74 | 28.39 (28.58 | 2.38 2.40 | 23.65 23.49 |

TABLE 10-continued

Structure: 5-R¹-6-(CH₂R²)-uracil (pyrimidine-2,4-dione with R¹ at 5-position and CH₂R² at 6-position)

| Comp'd No. | R¹ | R² | m.p. (° C.) Molecular formula | Yield (%) | Elemental analysis (%) Calculated (Found) C | H | N |
|---|---|---|---|---|---|---|---|
| 79 | Cl | 2-(methylthio)benzimidazole · HCl | 223 min. (decomp) C₁₂H₉N₄O₂SCl HCl | 81 | 41.75 (41.82 | 2.92 2.83 | 16.23 16.20 |
| 80 | Cl | 2-(methylthio)pyrimidine | 243 min. (decomp) C₉H₇N₄O₂SCl | 96 | 39.93 (40.01 | 2.61 3.11 | 20.70 20.47) |
| 81 | Cl | —NH–C(=S)–NHCH₃ | 195 min. (decomp) C₇H₉N₄O₂SCl 2/5H₂O | 61 | 32.86 (32.81 | 3.86 3.58 | 21.89 21.83) |
| 82 | Cl | —NH–C(=NCN)–NHCH₃ | 145 min. (decomp) C₈H₉N₆O₂Cl | 9 | 37.44 (37.27 | 3.53 3.50 | 32.74 33.03) |
| 83 | Cl | —NH–C(=O)–HN₂ | 225 min. (decomp) C₆H₇N₄O₃Cl H₂O | 9 | 30.46 (30.31 | 3.83 3.71 | 23.68 23.04) |

TABLE 11

Structure: 5-R¹-6-(CH₂R²)-uracil

| Comp'd No. | R¹ | R² | NMR spectrum (DMSO-d₆) δ |
|---|---|---|---|
| 1 | Cl | 1-methylpiperidine (N-methylpiperidin-yl) | 1.66–1.76(4H, m), 2.48–2.60(4H, m), 3.52(2H, s) |
| 2 | Br | 1-methylpiperidine | 1.64–1.79(4H, m), 2.52–2.63(4H, m), 3.55(2H, s) |
| 3 | I | 1-methylpiperidine | 1.64–1.79(4H, m), 2.49–2.57(4H, m), 3.57(2H, s) 11.36(1H, br-s) |

TABLE 11-continued
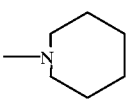
| Comp'd No. | R¹ | R² | NMR spectrum (DMSO-$d_6$) δ |
|---|---|---|---|
| 4 | CN | 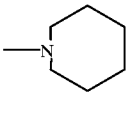 | 1.75–1.85(4H, m), 2.80–2.88(4H, m), 3.82(2H, s) |
| 5 | CH₃ |  | 1.67–1.75(4H, m), 1.78(3H, s), 2.45–2.55(4H, m), 3.38(2H, s) |
| 6 | Cl | 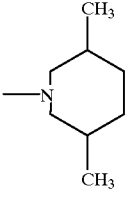 | 1.98(2H, quintet, J=7.0Hz), 3.27(4H, t, J=7.0Hz), 3.46(2H, s), 11.23(1H, br-s) |
| 7 | Cl | 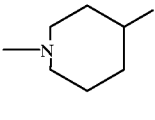 | 1.00(6H, d, J=5.9Hz), 1.38(2H, m), 1.83(2H, m), 2.67(2H, m), 3.59(2H, s) |
| 8 | Cl | 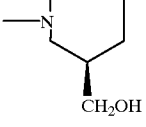 | 1.56(1H, m), 2.01(1H, m), 2.40–2.50(2H, m), 2.68–2.78(2H, m), 3.55(2H, s), 4.16(1H, m), 4.82(1H, br.s) |
| 9 | Cl | 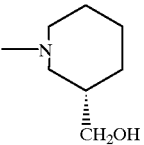 | 1.57–1.82(4H, m), 2.30(1H, q, J=8.0Hz), 2.65(1H, m), 2.92(1H, m), 3.30(1H, dd, J=11.3, 4.6Hz) 3.44(1H, dd, J=11.3, 3.8Hz), 3.55(1H, d, J=5.3Hz), 3.81(1H, d, J=5.3Hz), 4.72(1H, br.s), 11.46(1H, br.s) |
TABLE 12
| Comp'd No. | R¹ | R² | NMR spectrum (DMSO-$d_6$) δ |
|---|---|---|---|
| 10 | Cl | | 1.55–1.85(4H, m), 2.30(1H, q, J=7.8Hz), 2.65(1H, m), 2.92(1H, m), 3.25–3.27(1H, m), 3.44(1H, dd, J=11.2, 3.6Hz), 3.55(1H, d, J=5.3Hz), 3.81(1H, d, J=5.3Hz), 4.67(1H, br.s), 10.60(1H, br.s), 11.51(1H, br.s) |

TABLE 12-continued

| Comp'd No. | R¹ | R² | NMR spectrum (DMSO-$d_6$) δ |
|---|---|---|---|
| 11 | Cl | 1-methylpiperidin-3-amine ·2HCl | (in $D_2O$) 2.14(1H, m), 2.56(1H, m), 3.43–3.68(3H, m), 3.84(1H, dd, J=8.1, 12.7Hz), 4.13(1H, m), 4.37(2H, s) |
| 12 | Cl | 1-methyl-1,4,5,6-tetrahydropyrimidine | 2.61(2H, d, J=9.2Hz), 3.01(2H, d, J=9.2Hz), 3.94(2H, s), 6.92(1H, s), 11.49(1H, s), 11.57(1H, s) |
| 13 | Cl | 1-methylpiperidine | 1.32–1.56(6H, m), 2.34–2.46(4H, m), 3.36(2H, s), 11.11(1H, br, s) |
| 14 | Br | 1-methylpiperidine | 1.31–1.58(6H, m), 2.36–2.53(4H, m), 3.37(2H, s), 11.39(1H, br.s) |
| 15 | Cl | 1,4-dimethylpiperazine | 2.14(3H, s), 2.25–2.45(4H, br.s), 2.45–2.55(4H, br.s), 3.33(2H, s) |
| 16 | Cl | 4-methylmorpholine | 2.44–2.47(4H, m), 3.40(2H, s), 3.56–3.60(4H, m), 10.84(1H, br.s), 11.53(1H, br.s) |
| 17 | Cl | 1-methylazepane | 1.51–1.66(8H, m) 2.62–2.70(4H, m), 3.54(2H, s) |
| 18 | Cl | 1-methylazocane | 1.45–1.63(10H, m), 2.55–2.65(4H, m), 3.49(2H, s) |

TABLE 13

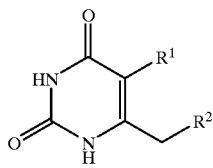

| Comp'd No. | R¹ | R² | NMR spectrum (DMSO-d₆) δ |
|---|---|---|---|
| 19 | Cl | —CH₂—N(piperidine) | (in CDCl₃) 1.89(4H, quintet, J=3.3Hz), 2.68(4H, t, J=3.3Hz), 2.82(2H, m), 2.93(2H, m), 3.64(2H, s) |
| 20 | Cl | (N-methyl tetrahydropyrimidinimine·HCl, NCH₃) | 3.46(3H, s), 5.04(2H, s), 7.06(1H, d, J=11.4Hz), 7.07(1H, d, J=11.4Hz), 8.11(2H, br-s), 11.38(1H, br-s), 11.70(1H, s) |
| 21 | Cl | (N-methyl tetrahydropyrimidinimine·HCl, NC₂H₅) | 1.26(3H, J=7.2Hz), 3.89(2H, q, J=7.2Hz), 5.06(2H, s), 7.07(1H, d, J=2.6Hz), 7.15(1H, d, J=2.6Hz), 8.19(1H, s), 11.47(1H, s), 11.72(1H, s) |
| 22 | Cl | (N-methylpiperidin-4-yl methanesulfonate) | 1.92(1H, m), 2.26(1H, m), 2.51(1H, m), 2.79–2.94(3H, m), 3.18(3H, s), 3.56(2H, s), 5.15(1H, m), 10.94(1H, br.s), 11.54(1H, br.s) |
| 23 | Cl | (2-nitroimino-1,3,5-triazinane, N-methyl) | 5.44(2H, s), 8.99(1H, s), 11.55–11.65(1H, br.s), 11.79(1H, br.s) |
| 24 | Cl | (N-methyl dihydropyrimidine) | 5.17(2H, s), 6.29(1H, dd, J=2.3, 1.5Hz), 7.50(1H, d, J=1.5Hz), 7.86(1H, d, J=2.3Hz), 11.53(1H, s), 11.68(1H, s) |
| 25 | Cl | (N-methyl-2-methyl dihydropyrimidine·HCl) | 2.60(3H, s), 5.22(2H, s), 7.54(1H, d, J=2.0Hz), 7.61(1H, d, J=2.0Hz), 11.77(1H, s) |

TABLE 14

| Comp'd No. | R¹ | R² | NMR spectrum (DMSO-$d_6$) δ |
|---|---|---|---|
| 26 | Cl | 1-methyl-2-nitro-1,6-dihydropyrimidine (N-CH₂– linked) | 5.54(2H, s), 7.23(1H, d, J=1.2Hz), 7.68(1H, d, J=1.2Hz), 11.20–11.60(1H, br.s), 11.70(1H, s) |
| 27 | Cl | 1-methyl-5-nitro-1,6-dihydropyrimidine | 5.18(2H, s), 7.95(1H, d, J=1.3Hz), 8.43(1H, d, J=1.3Hz), 11.50(1H, s), 11.70(1H, s) |
| 28 | Cl | 1-methyl-1,6-dihydro-1,3,5-triazine | 5.26(2H, s), 8.03(1H, s), 8.64(1H, s), 11.57(1H, s), 11.70(1H, s) |
| 29 | Cl | 2-imino-piperidinyl·HCl | 2.04(2H, quintet, J=7.6Hz), 2.87(2H, t, J=7.6Hz), 3.59(2H, t, J=7.6Hz), 4.69(2H, s), 9.40(1H, s) 9.75(1H, s), 11.46(1H, s), 11.73(1H, s) |
| 30 | Cl | 2-imino-piperidinyl·TsOH | 2.05(2H, quintet, J=7.7Hz), 2.29(3H, s), 2.87(2H, t, J=7.7Hz), 3.60(2H, t, J=7.7Hz), 4.56(2H, s), 7.11(2H, d, J=7.3Hz), 7.47(2H, d, J=7.3Hz) 9.51(1H, br-s), 11.0–11.8(2H, very br) |
| 31 | Br | 2-imino-piperidinyl·HCl | 2.05(2H, quintet, J=7.4Hz), 2.86(2H, t, J=7.4Hz), 3.59(2H, t, J=7.4Hz), 4.63(2H, s), 9.29(1H, br-s), 9.68(1H, br-s), 11.44(1H, s), 11.69(1H, s) |
| 32 | CH₃ | 2-imino-piperidinyl·HCl | 1.76(3H, s), 2.02(2H, quintet, J=7.6Hz), 2.84(2H, t, J=7.6Hz), 3.51(2H, t, J=7.6Hz), 4.55(2H, s) |
| 33 | CN | 2-imino-piperidinyl | 2.07(2H, quintet, J=7.6Hz), 2.89(2H, t, J=7.6Hz), 3.65(2H, t, J=7.6Hz), 4.50(2H, s), |

TABLE 15

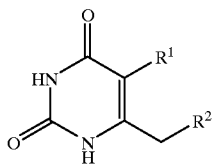

| Comp'd No. | R¹ | R² | NMR spectrum (DMSO-$d_6$) δ |
|---|---|---|---|
| 34 | Cl | (N-methylpiperazin-2-imine, N'-CH₃) | 2.92(3H, s), 3.57(4H, s), 4.27(2H, s) |
| 35 | Cl | (N-methylpiperazin-2-imine, N'-C₂H₅) | 1.11(3H, t, J=7.3Hz), 3.35(2H, q, J=7.3Hz), 3.59(4H, s), 4.26(2H, s), 9.76(1H, s) |
| 36 | Cl | (N-methylpiperazin-2-imine, N'-CH(CH₃)₂) | 1.15(6H, d, J=6.3Hz), 3.48–3.62(4H, m), 4.04(1H, septet, J=6.3Hz), 4.26(2H, s) |
| 37 | Cl | —NH(CH₂)₂NH₂ | 2.57–2.72(4H, m), 3.59(2H, s) |
| 38 | Br | —NH(CH₂)₂NH₂ | 2.63–2.75(4H, m), 3.58(2H, s) |
| 39 | I | —NH(CH₂)₂NH₂ | 2.58–2.72(4H, m), 3.58(2H, s) |
| 40 | Cl | —NH—N(CH₃)₂·HCl | 3.39(6H, s), 4.67(2H, s), 6.48(2H, s), 11.49(1H, s), 11.84(1H, s) |
| 41 | Cl | —NH(CH₂)₂N(CH₃)₂ | 2.83(6H, s), 3.42(4H, s), 4.12(2H, s), 8.42(1H, br.s), 11.76(1H, br.s) |
| 42 | Cl | —NH(CH₂)₃NH₂ | 1.59(2H, quintet, J=6.1Hz), 2.58(2H, t, J=6.1Hz), 2.83(2H, t, J=6.1Hz), 3.55(2H, s) |
| 43 | Cl | —NH(CH₂)₂CN | 2.61(2H, t, J=6.4Hz), 2.74(2H, t, J=6.4Hz), 3.66(2H, s), 6.66(1H, br.s) |

TABLE 16

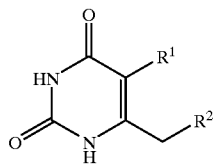

| Comp'd No. | R¹ | R² | NMR spectrum (DMSO-$d_6$) δ |
|---|---|---|---|
| 44 | Cl | —NH(CH₂)₃OH | 1.55(2H, quintet, J=6.6Hz), 2.54(2H, t, J=6.6Hz), 3.44(2H, t, J=6.6Hz), 3.63(2H, s) |
| 45 | Cl | —N(CH₃)(CH₂)₂OH | 2.21(3H, s), 2.49–2.53(2H, m), 3.48(2H, t, J=5.4Hz), 3.52(2H, s), 4.73(1H, br.s), 10.60(1H, br.s), 11.52(1H, br.s) |
| 46 | Cl | —NH(CH₂)₄OH | 1.38–1.48(4H, m), 2.46–2.51(2H, m), 3.38(2H, t, J=5.6Hz), 3.63(2H, s) |

TABLE 16-continued

| Comp'd No. | R¹ | R² | NMR spectrum (DMSO-d₆) δ |
|---|---|---|---|
| 47 | Cl | (1-methyl-2-imino-hexahydropyrimidine) | 3.45–3.70(4H, s), 4.26(2H, s) |
| 48 | Br | (1-methyl-2-imino-hexahydropyrimidine) | 3.48–3.68(4H, s), 4.25(2H, s) |
| 49 | I | (1-methyl-2-imino-hexahydropyrimidine) | 3.45–3.68(4H, m), 4.22(2H, s) |
| 50 | Cl | (1-methyl-1,4,5,6-tetrahydropyrimidine) · HCl | 3.78–3.98(4H, m), 4.60(2H, s) 8.59(1H, s), 10.90(1H, br-s), 11.71(1H, s) |
| 51 | Cl | (1-methylpyrimidine) · HCl | 5.40(2H, s), 7.74(1H, d, J=1.3(Hz), 7.82(1H, d, J=1.3Hz), 9.29(1H, s), 11.74(1H, s), 11.78(1H, br-s) |
| 52 | Cl | (1-methyl-triazine) | 5.45(2H, s), 7.79(1H, s), 8.26(1H, s), 11.69(1H, s), 11.74(1H, s) |
| 53 | Cl | S-methyl isothiourea · HCl | 4.35(2H, s), 9.46(4H, br-s), 11.57(1H, br-s), 11.70(1H, br-s) |

TABLE 17

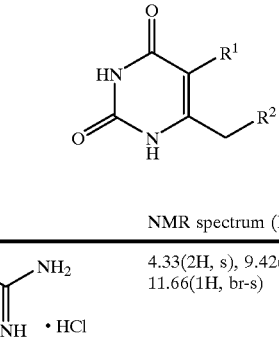

| Comp'd No. | R¹ | R² | NMR spectrum (DMSO-d$_6$) δ |
|---|---|---|---|
| 54 | Br | 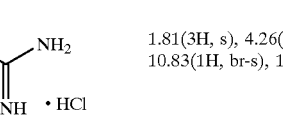 | 4.33(2H, s), 9.42(4H, br-s), 11.60(1H, br-s), 11.66(1H, br-s) |
| 55 | CH$_3$ | 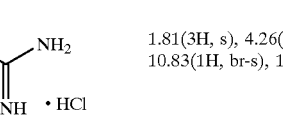 | 1.81(3H, s), 4.26(2H, s), 9.39(4H, br-s), 10.83(1H, br-s), 11.18(1H, br-s) |
| 56 | CN | 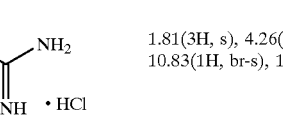 | 4.33(2H, s) |
| 57 | Cl | 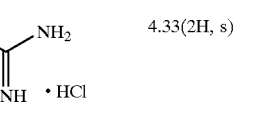 | 2.90(3H, s), 4.32(2H, s), 9.40(1H, br-s), 9.77(1H, br-s), 10.20(1H, br-s), 11.51(1H, br-s), 11.67(1H, br-s) |
| 58 | Cl | 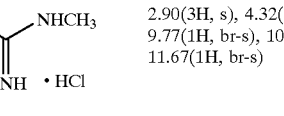 | 2.93(3H, s), 3.03(3H, s), 4.27(2H, s), 9.60(1H, br-s), 9.94(1H, br-s), 11.53(1H, br-s), 11.67(1H, br-s) |
| 59 | Cl | —NH$_2$ | 3.60(2H, s) |
| 60 | Cl | —NHCH$_3$ | 2.27(3H, s), 3.61(2H, s) |
| 61 | Cl | —N(CH$_3$)$_2$ | 2.22(6H, s), 3.33(2H, s), 11.41(1H, br.s) |
| 62 | Cl | —NHC$_2$H$_5$ | 1.02(3H, t, J=7.1Hz), 2.53(2H, q, J=7.1Hz), 3.64(2H, s) |
| 63 | Cl | —N(C$_2$H$_5$)$_2$ | 0.97(6H, t, J=7.1Hz), 2.55(4H, q, J=7.1Hz), 3.49(2H, s) |

TABLE 18

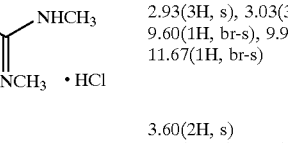

| Comp'd No. | R¹ | R² | NMR spectrum (DMSO-d$_6$) δ |
|---|---|---|---|
| 64 | Cl | —NH(CH$_2$)$_2$CH$_3$ | 0.86(3H, t, J=7.3Hz), 1.41(2H, tq, J=7.3, 7.3Hz), 2.44(2H, t, J=7.3Hz), 3.63(2H, s), 8.05(1H, br.s) |
| 65 | Cl | —NHCH(CH$_3$)$_2$ | 0.99(6H, d, J=6.1Hz), 2.70(1H, sept, J=6.1Hz), 3.64(2H, s) |
| 66 | Cl | —CH$_2$NHCH$_3$ | 2.32(3H, s), 2.67(2H, d, J=6.4Hz), 2.79(2H, d, J=6.4Hz) |
| 67 | Cl | —CH$_2$N(CH$_3$)$_2$ | (in CDCl$_3$) 2.36(6H, s), 2.71–2.82(4H, m) |

TABLE 18-continued

[Structure: pyrimidine-2,4-dione with R¹ at 5-position and CH₂R² at 6-position]

| Comp'd No. | R¹ | R² | NMR spectrum (DMSO-d₆) δ |
|---|---|---|---|
| 68 | Cl | [MeNH-C(=NH)-NH₂ · HCl] | 4.29(2H, d, J=5.0Hz), 7.45(3H, br-s), 7.99(1H, t, J=5.0Hz), 11.45(1H, br-s), 11.64(1H, br-s) |
| 69 | Cl | [Me(CH₃)N-C(=NH)-NH₂] | 2.88(3H, s), 4.48(2H, s), 7.65(4H, s), 11.39(1H, br-s), 11.63(1H, br-s) |
| 70 | Cl | [MeNH-C(=NH)-NHCH₃ · HCl] | 2.54(3H, d, J=4.6Hz), 4.28(2H, d, J=5.5Hz), 7.57(1H, br-s), 7.74–7.82(2H, m), 11.37(1H, br-s), 11.66(1H, s) |
| 71 | Cl | [MeNH-C(=NCH₃)-NHCH₃ · HCl] | 2.77(6H, d, J=4.6Hz), 4.32(2H, d, J=5.6Hz), 7.66–7.80(3H, m), 11.29(1H, s), 11.67(1H, s) |
| 72 | Cl | [—NH-(2-imidazolinyl) · HCl] | 3.62(4H, s), 4.38(2H, d, J=5.6Hz), 8.45(1H, br.s), 8.69(1H, t, J=5.6Hz), 11.44(1H, s), 11.67(1H, s) |

TABLE 19

[Structure: pyrimidine-2,4-dione with R¹ at 5-position and CH₂R² at 6-position]

| Comp'd No. | R¹ | R² | NMR spectrum (DMSO-d₆) δ |
|---|---|---|---|
| 73 | Cl | [MeNH-C(=NH)-CH₃ · HCl] | 2.19(3H, s), 4.40(2H, d, J=5.0Hz), 9.13(1H, s), 9.63(1H, s), 9.86(1H, d, J=5.0Hz), 11.53(1H, s), 11.73(1H, s) |
| 74 | Cl | [N-methyl dihydropyridine] | 4.92(2H, s), 6.04(2H, d, J=1.8Hz), 6.87(2H, d, J=1.8Hz), 11.61(2H, br.s) |

TABLE 19-continued

[Structure: pyrimidine-2,4-dione with R¹ at 5-position and CH₂R² at 6-position]

| Comp'd No. | R¹ | R² | NMR spectrum (DMSO-d₆) δ |
|---|---|---|---|
| 75 | Cl | -S-(2-imidazolyl) ·HCl | 4.03(2H, s), 7.81(2H, s), 11.30–11.50(1H, br.s), 11.60(1H, s) |
| 76 | Cl | -S-(2-imidazolyl) ·HCl | 3.34(4H, s), 4.41(2H, s), 10.50–10.70(1H, br.s), 11.70(1H, s) |
| 77 | Cl | -S-(1-methyl-2-imidazolyl) ·HCl | 3.88(3H, s), 3.99(2H, s), 7.77(1H, d, J=1.7Hz), 7.90(1H, d, J=1.7Hz), 11.41(1H, s), 11.60(1H, s) |
| 78 | Cl | -S-(1,2,4-triazol-3-yl) ·HCl | 4.11(2H, s), 8.55(1H, s), 11.33(1H, s), 11.58(1H, s) |
| 79 | Cl | -S-(2-benzimidazolyl) ·HCl | 4.35(2H, s), 7.33–7.63(4H, m), 11.63(1H, s) |
| 80 | Cl | -S-(2-pyrimidinyl) | 4.31(2H, s), 7.30(1H, t, J=5.0Hz), 8.69(2H, d, J=5.0Hz), 11.36(1H, s), 11.61(1H, s) |

TABLE 20

[Structure: pyrimidine-2,4-dione with R¹ at 5-position and CH₂R² at 6-position]

| Comp'd No. | R¹ | R² | NMR spectrum (DMSO-d₆) δ |
|---|---|---|---|
| 81 | Cl | -NH-C(=S)-NHCH₃ | 2.77–2.87(3H, br.s), 4.49–4.54(2H, br.s), 7.55–8.20(2H, br.s), 10.80–11.00(1H, br.s), 11.55–11.65(1H, br.s) |

TABLE 20-continued

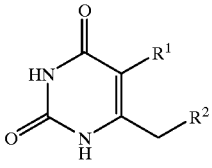

| Comp'd No. | R¹ | R² | NMR spectrum (DMSO-$d_6$) δ |
|---|---|---|---|
| 82 | Cl | —NH-C(=NCN)-NHCH₃ | 2.72(3H, d, J=3.6Hz), 4.21(2H, d, J=4.6Hz), 7.17–7.35(2H, m), 11.03(1H, s), 11.58(1H, s) |
| 83 | Cl | —NH-C(=O)-HN₂ | 4.09(2H, d, J=5.9Hz), 5.86(2H, s), 6.40(1H, t, J=5.9Hz), 10.70–10.95(1H, br.s), 11.54(1H, s) |

| Preparation Example 1 (Antitumor Effect Potentiator) | |
|---|---|
| Compound 29 | 25.0 mg |
| Lactose | 8.0 |
| Crystalline cellulose | 4.0 |
| Magnesium stearate | 1.0 |
| Talc | 1.0 |
| Corn starch | 3.5 |
| Hydroxypropyl methylcellulose | 2.5 |
| Tablet | 45.0 mg |

In accordance with the above formula, tablets were prepared in a manner known per se in the art.

| Preparation Example 2 (Antitumor Effect Potentiator) | |
|---|---|
| Compound 29 | 50.0 mg |
| Lactose | 85.0 |
| Corn starch | 100.0 |
| Hydroxypropyl cellulose | 3.0 |
| Granules | 238.0 mg |

In accordance with the above formula, granules were prepared in a manner known per se in the art.

| Preparation Example 3 (Antitumor Effect Potentiator) | |
|---|---|
| Compound 29 | 50.0 mg |
| Lactose | 24.0 |
| Crystalline cellulose | 13.0 |
| Magnesium stearate | 1.0 |
| Capsule | 88.0 mg |

In accordance with the above formula, capsules were prepared in a manner known per se in the art.

| Preparation Example 4 (Antitumor Agent) | |
|---|---|
| 5-Trifluoromethyl-2'-deoxyuridine ($F_3$dThd) | 12.5 mg |
| Compound 29 | 25.0 mg |
| Lactose | 8.0 |
| Crystalline cellulose | 3.5 |
| Magnesium stearate | 1.0 |
| Talc | 1.0 |
| Corn starch | 3.5 |
| Hydroxypropyl methylcellulose | 2.5 |
| (Per tablet) | 57.0 mg |

In accordance with the above formula, tablets were prepared in a manner known per se in the art.

| Preparation Example 5 (Antitumor Agent) | |
|---|---|
| 5-Trifluoromethyl-2'-deoxyuridine ($F_3$dThd) | 12.5 mg |
| Compound 29 | 50.0 mg |
| Lactose | 85.0 |
| Corn starch | 100.0 |
| Hydroxypropyl cellulose | 2.5 |
| (Per bag) | 250.0 mg |

In accordance with the above formula, granules were prepared in a manner known per se in the art.

| Preparation Example 6 (Antitumor Agent) | |
|---|---|
| 5-Trifluoromethyl-2'-deoxyuridine ($F_3$dThd) | 12.5 mg |
| Compound 29 | 50.0 mg |
| Lactose | 24.0 |
| Crystalline cellulose | 12.5 |
| Magnesium stearate | 1.0 |
| (Per capsule) | 100.0 mg |

In accordance with the above formula, capsules were prepared in a manner known per se in the art.

Test 1 (Thymidine Phosphorylase Inhibiting Effects)

Inhibitory effects of some uracil derivatives (I) or salts thereof on thymidine phosphorylase were each determined by measuring the formation of [6-$^3$H]thymine from [6-$^3$H] thymidine in the below-described manner.

Namely, reacted at 37° C. for 5 minutes were 0.05 ml of a 3 mM aqueous solution of thymidine (which contained 74 Bq/ml of [6-$^3$H]thymidine), 0.05 ml of a 0.5 M potassium phosphate buffer (pH 7.4), 0.05 ml of a solution of one of the test compounds at one of various concentrations or purified water as a control, and 0.1 ml of a solution of thymidine phosphorylase obtained from human placenta in a highly purified form, 0.25 ml in total. Immediately after the reaction, the reaction mixture was heated for 2 minutes in a boiling water bath of 100° C. to terminate the reaction, followed by centrifugation at 3000 rpm for 10 minutes. Subsequent to the centrifugation, a portion (10 μl) of the resultant supernatant was spotted on a silica gel 60F$_{254}$ plate of 2.0×10 cm and was then dried in air. The plate was placed in a developer bath which was filled with chloroform-methanol-acetic acid (v/v/v, 17:3:1), so that the spot was developed to a position of about 8 cm. The silica gel plate was pulled out and then dried in air. Under a UV lamp, a position (R$_f$ 0.46) of [6-$^3$H]thymine was marked. Silica gel was scraped off from the position by a stainless steel spatula and then placed in a vial for liquid scintillation. One hundred microliters of 2 N HCl were added to moisten the silica gel, whereby [6-$^3$H]thymine was liberated from the gel. Thereafter, 10 ml of scintillator ("AQUASOL-II", product of Amersham International plc) were added, followed by thorough agitation with a stirrer. Radioactivity was then measured by a scintillation counter ("WALLAC SYSTEM 1410", manufactured by Pharmacia AB).

Inhibitory activities of the test compound were determined by the following formula:

$$\text{Inhibition rate (\%)} = \left\{1 - \frac{\text{Amount of [6-}^3\text{H] thymine in the presence of the test solution (dpm)} - \text{Blank (dpm)}}{\text{Amount of [6-}^3\text{H] thymine in the control (dpm)} - \text{Blank (dpm)}}\right\} \times 100$$

The concentration of each test solution which inhibited 50% of the amount of [6-$^3$H]thymine formed by thymidine phosphorylase is shown as IC$_{50}$ (μM) in Table 21.

To compare inhibitory activities, IC$_{50}$s of 6-amino-5-chlorouracil, 6-amino-5-bromouracil, 6-aminothymine, acy-clothymidine and 3-cyano-2,6-dihydroxypyrimidine were also measured and calculated.

TABLE 21

| Compound No. or Compound Name | IC$_{50}$ (μM) |
|---|---|
| 1 | 2.2 |
| 2 | 0.51 |
| 3 | 1.3 |
| 6 | 2.6 |
| 20 | 0.24 |
| 29 | 0.035 |
| 32 | 0.12 |
| 33 | 0.017 |
| 34 | 0.046 |

TABLE 21-continued

| Compound No. or Compound Name | IC$_{50}$ (μM) |
|---|---|
| 47 | 0.013 |
| 48 | 0.030 |
| 50 | 1.2 |
| 51 | 1.0 |
| 53 | 0.35 |
| 56 | 0.10 |
| 57 | 0.15 |
| 68 | 0.27 |
| 73 | 1.5 |
| 6-Amino-5-chlorouracil | 12 |
| 6-Amino-5-bromouracil | 19 |
| 6-Aminothymine | 100 |
| Acyclothymidine | >1000 |
| 3-Cyano-2,6-dihydroxypyridine | 130 |

Test 2 (Antitumor Effects)

(a) Preparation of the test solution I:

F$_3$dThd was suspended in portions of a 0.5% solution of hydroxypropyl methylcellulose so that its concentrations became 5.0 mg/ml and 10.0 mg/ml. They were separately agitated by stirrers at room temperature for about 20 minutes and then subjected to ultrasonic treatment for 5 minutes under ice cooling, whereby drug solutions [test solutions (1),(2)] were obtained for the single administration of F$_3$dThd.

(b) Preparation of test solutions II:

F$_3$dThd was suspended in a 0.5% solution of hydroxypropyl methylcellulose so that its concentration became 7.5 mg/ml. To portions of the suspension, one of some uracil derivatives (1) or a salt thereof (Compounds 2, 29, 47 and 48) was added so that its concentrations became 6.9, 7.0, 6.9 and 7.5 mg/ml. The resultant mixtures were separately agitated at room temperature for about 20 minutes by stirrers and then subjected to ultrasonic treatment under ice cooling, whereby mixed solutions [test solutions (3) to (6)] according to the present invention were obtained.

(c) Test:

Nude-mouse-transplanted human tumor sections of about 2 mm square were subcutaneously transplanted to axillary fossae of nude mouse of 4 to 5 weeks old. When an estimated tumor volume as determined by V=1/2×L (major axis)×(minor axis)×Q (thickness) reached about 150 mm$^3$, a control group and treated groups were set so that the averages and standard deviations (S.D.) of tumors in the individual treated groups became as equal as possible. Administration of the drugs was then started.

The administration was conducted by orally administering the test solutions (1) to (6) in an amount of 1.0 ml per 100 g of the body weight of each nude mouse once a day for 14 days. The tumor-bearing rats in the control group were orally administered only with a 0.5% solution of hydroxypropyl methylcellulose.

Upon an elapsed time of 24 hours after the final administration of each drug, the above-described estimated tumor volume (V) was determined. In accordance with the below-described formula, a tumor size reduction rate (%) was then determined and is shown in

TABLE 22

$$\text{Tumor size reduction rate} = \left(1 - \frac{\text{Tumor volume of the test-solution-administered group (mm}^3\text{)}}{\text{Tumor volume of the control group (mm}^3\text{)}}\right) \times 100$$

TABLE 22

| Test solution | Drug | Dose* (mg/kg) | Tumor size reduction rate (%) |
|---|---|---|---|
| 1 | F$_3$dThd | 50 | 27 |
| 2 |  | 100 | 50 |
| 3 | F$_3$dThd + Comp'd 2 | 75 | 66 |
| 4 | F$_3$dThd + Comp'd 29 | 75 | 61 |
| 5 | F$_3$dThd + Comp'd 47 | 75 | 56 |
| 6 | F$_3$dThd + Comp'd 48 | 75 | 46 |

*in terms of the amount of F$_3$dThd.

Test 3 (Antitumor Effects)

(a) Preparation of test solutions I:

F$_3$dThd was suspended in portions of a 0.5% solution of hydroxypropyl methylcellulose so that its concentrations became 1.25, 2.5, 5.0, 7.5 and 10.0 mg/ml. Thy were separately agitated by stirrers at room temperature for about 20 minutes and then subjected to ultrasonic treatment for 5 minutes under ice cooling, whereby drug solutions [test solutions (1) to (5)] were obtained for the single administration of F$_3$dThd.

(b) Preparation of test solutions II:

F$_3$dThd was suspended in portions of a 0.5% solution hydroxypropyl methylcellulose so that its concentrations became 1.25, 2.5, 5.0, 7.5 and 10 mg/ml. Compound 29 was added to the individual suspensions so that its concentrations became 0.23, 0.46, 0.93, 1.39 and 1.85 mg/ml, respectively. The resultant mixtures were separately agitated at room temperature for about 20 minutes by stirrers and then subjected to ultrasonic treatment for 5 minutes under ice cooling, whereby F$_3$dThd-Compound 29 (molar ratio: 1:0.2) mixed solutions [test solutions (6) to (10)] were obtained.

(c) Preparation of test solutions III:

F$_3$dThd-Compound 29 (molar ratio: 1:0.5) mixed solutions [test solutions (11) to (15)] were obtained in a similar manner as the preparation of the above test solutions except that the amount of Compound 29 was set at 0.58, 1.16, 2.31, 3.47 and 4.63 mg/ml.

(d) Preparation of test solutions IV:

F$_3$dThd-Compound 29 (molar ratio: 1:1) mixed solutions [test solutions (16) to (20)] were obtained in a similar manner as the preparation of the above test solutions except that the amount of Compound 29 was set at 1.16, 2.31, 4.63, 6.94 and 9.25 mg/ml.

(e) Preparation of test solutions V:

F$_3$dThd-Compound 29 (molar ratio: 1:2) mixed solutions [test solutions (21) to (25)] were obtained in a similar manner as the preparation of the above test solutions except that the amount of Compound 29 was set at 2.31, 4.63, 9.25, 13.88 and 18.51 mg/ml.

(f) Preparation of test solutions VI:

F$_3$dThd-Compound 29 (molar ratio: 1:5) mixed solutions [test solutions (26) to (30)] were obtained in a similar manner as the preparation of the above test solutions except that the amount of Compound 29 was set at 5.78, 11.57, 23.14, 34.70 and 46.27 mg/ml.

(g) Test:

A test was conducted in a similar manner as Test 2 except for the use of the test solutions (1) to (30).

Further, the body weight was periodically measured from the 24th hour after the last day of the drug administration to determine body weight changes (BWCs) relative to the body weight before the initiation of the drug administration. In accordance with the following formula, a therapeutic index (TI) was then determined and is shown in Table 23.

$$\text{Therapeutic Index (TI)} = \frac{\begin{array}{c}\text{Concentration of F}_3\text{dThd providing a} \\ \text{10\% reduction in body weight compared} \\ \text{with the control group (BCW}_{-10}) \end{array}}{\begin{array}{c}\text{Concentration of F}_3\text{dThd providing a} \\ \text{50\% inhibition against a tumor weight} \\ \text{increase compared with the control} \\ \text{group (ED}_{50}) \end{array}}$$

TABLE 23

| Test solution | Drug (molar ratio) | Dose* (mg/kg) | ED$_{50}$ (mg/kg) | BWC$_{-10}$ (mg/kg) | Therapeutic index BWC$_{-10}$/ED$_{50}$ |
|---|---|---|---|---|---|
| 1 | Administration | 12.5 | 26.9 | 73.8 | 2.7 |
| 2 | of | 25.0 | | | |
| 3 | F$_3$dThd alone | 50.0 | | | |
| 4 |  | 75.0 | | | |
| 5 |  | 100.0 | | | |
| 6 | F$_3$dThd | 12.5 | 5.6 | >100 | >17.9 |
| 7 | + | 25.0 | | | |
| 8 | Compound 29 | 50.0 | | | |
| 9 | (1:0.2) | 75.0 | | | |
| 10 |  | 100.0 | | | |
| 11 | F3dThd | 12.5 | 7.9 | >100 | >12.7 |
| 12 | + | 25.0 | | | |
| 13 | Compound 29 | 50.0 | | | |
| 14 | (1:0.5) | 75.0 | | | |
| 15 |  | 100.0 | | | |
| 16 | F$_3$dThd | 12.5 | 7.8 | >100 | >12.8 |
| 17 | + | 25.0 | | | |
| 18 | Compound 29 | 50.0 | | | |
| 19 | (1:1) | 75.0 | | | |
| 20 |  | 100.0 | | | |
| 21 | F$_3$dThd | 12.5 | 8.7 | >100 | >11.5 |
| 22 | + | 25.0 | | | |
| 23 | Compound 29 | 50.0 | | | |
| 24 | (1:2) | 75.0 | | | |
| 25 |  | 100.0 | | | |
| 26 | F$_3$dThd | 12.5 | 10.1 | >100 | >9.9 |
| 27 | + | 25.0 | | | |
| 28 | Compound: 29 | 50.0 | | | |
| 29 | (1:5) | 75.0 | | | |
| 30 |  | 100.0 | | | |

*in terms of the amount of F$_3$dThd.

Test 4 (Antitumor Effects)

A test was conducted in a similar manner as Test 3 except for the use of Compound 2 instead of Compound 29. The results are shown in Table 24.

TABLE 24

| Test solution | Drug (molar ratio) | Dose* (mg/kg) | ED$_{50}$ (mg/kg) | BWC$_{-10}$ (mg/kg) | Therapeutic index BWC$_{-10}$/ED$_{50}$ |
|---|---|---|---|---|---|
| 1 | Administration | 12.5 | 60.0 | 103 | 1.7 |
| 2 | of | 25.0 | | | |
| 3 | F$_3$dThd alone | 50.0 | | | |

TABLE 24-continued

| Test solution | Drug (molar ratio) | Dose* (mg/kg) | $ED_{50}$ (mg/kg) | $BWC_{-10}$ (mg/kg) | Therapeutic index $BWC_{-10}/ED_{50}$ |
|---|---|---|---|---|---|
| 4 | | 75.0 | | | |
| 5 | | 100.0 | | | |
| 6 | $F_3$dThd | 12.5 | 43.0 | 87 | 2.0 |
| 7 | + | 25.0 | | | |
| 8 | Compound 2 | 50.0 | | | |
| 9 | (1:0.2) | 75.0 | | | |
| 10 | | 100.0 | | | |
| 11 | F3dThd | 12.5 | 35.0 | 82 | 2.3 |
| 12 | + | 25.0 | | | |
| 13 | Compound 2 | 50.0 | | | |
| 14 | (1:0.5) | 75.0 | | | |
| 15 | | 100.0 | | | |
| 16 | $F_3$dThd | 12.5 | 12.0 | 85 | 7.1 |
| 17 | + | 25.0 | | | |
| 18 | Compound 2 | 50.0 | | | |
| 19 | (1:1) | 75.0 | | | |
| 20 | | 100.0 | | | |
| 21 | $F_3$dThd | 12.5 | 10.5 | 48 | 4.6 |
| 22 | + | 25.0 | | | |
| 23 | Compound 2 | 50.0 | | | |
| 24 | (1:2) | 75.0 | | | |
| 25 | | 100.0 | | | |
| 26 | $F_3$dThd | 12.5 | 16.5 | 43 | 2.0 |
| 27 | + | 25.0 | | | |
| 28 | Compound: 2 | 50.0 | | | |
| 29 | (1:5) | 75.0 | | | |
| 30 | | 100.0 | | | |

*in terms of the amount of $F_3$dThd.

Test 5 (Antitumor Effects)

(a) Preparation of test solutions I:

5-Fluoro-2'-deoxyuridine (FdUrd) was suspended in portions of a 0.5% solution of hydroxypropyl methylcellulose so that its concentrations became 0.5 mg/ml and 1.0 mg/ml, respectively. The suspensions were separately agitated by stirrers at room temperature for about 20 minutes and then subjected to ultrasonic treatment under ice cooling for 5 minutes, whereby test solutions (1) and (2) were obtained.

(b) Preparation of test solutions II:

Compound 2 and Compound 29 were separately suspended in portions of the test solution (1) so that their concentrations became 0.83 mg/ml and 0.81 mg/ml, respectively. The suspensions were separately agitated by stirrers at room temperature for about 20 minutes and then subjected to ultrasonic treatment under ice cooling for 5 minutes, whereby test solutions (3) and (4) were obtained.

(c) Preparation of test solutions III:

Compound 2 and Compound 29 were separately suspended in portions of the test solution (2) so that their concentrations became 4.15 mg/ml and 4.05 mg/ml, respectively. The suspensions were separately agitated by stirrers at room temperature for about 20 minutes and then subjected to ultrasonic treatment under ice cooling for 5 minutes, whereby test solutions (5) and (6) were obtained.

(c) Test:

S-180 cells ($1 \times 10^7$ cells) were subcutaneously transplanted to the backs of ICR male mice of 5 weeks old. After an elapsed time of 24 hours from the transplant, one of the above-described test solutions (1) to (6) was orally administered once a day in an amount of 0.1 ml per 10 g of the body weight of the mouse for 7 days. A 0.5% solution of hydroxypropyl methylcellulose alone was orally administered to each tumor-bearing mouse in a control group. On the 10th day after the transplant of the tumor, the mouse was sacrificed, and the tumor was enucleated and its weight was measured. In accordance with the following formula, a tumor size reduction rate (%) was determined and is shown in Table 25.

Tumor size reduction rate (%) =

$$\left(1 - \frac{\text{Tumor volume of the test-solution-administered group (g)}}{\text{Tumor volume of the control group (g)}}\right) \times 100$$

TABLE 25

| Test solution | Drug (molar ratio) | Dose* (mg/kg) | Tumor size reduction rate (%) |
|---|---|---|---|
| 1 | FdUrd | 5 | 10.5 |
| 2 | | 10 | 24.4 |
| 3 | FdUrd + Comp'd 2 (1:1) | 5 | 46.4 |
| 5 | FdUrd + Comp'd 2 (1:5) | 5 | 48.2 |
| 4 | FdUrd + Comp'd 29 (1:1) | 5 | 58.8 |
| 6 | FdUrd + Comp'd 29 (1:5) | 5 | 47.2 |

*in terms of the amount of FdUrd.

Capability of Exploitation in Industry

The uracil derivatives of the formula (1) and their salts have the merits that they have extremely great thymidine phosphorylase inhibiting activities compared with conventionally-known thymidine phosphorylase inhibitors and substantially enforce antitumor effects of 2'-deoxypyrimidine nucleosides. Accordingly, antitumor effect potentiator and antitumor agent according to the present invention have extremely high utility.

What is claimed is:

1. A uracil derivative represented by the following formula (1'):

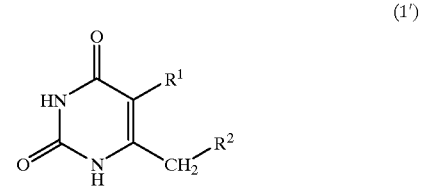

(1')

wherein $R^1$ is selected from the group consisting of chlorine, bromine, iodine, cyano and a lower alkyl group; and $R^2$ represents an amidinothio group, one or more of the hydrogen atom(s) on one or both of the nitrogen atoms of which may each be substituted by a lower alkyl group; a guanidino group, one or more of the hydrogen atom(s) on one, two or all of the nitrogen atoms of which may each be substituted by a lower alkyl or cyan group; a (lower alkyl) amidino group; a group —$CH_2N(R^a)R^b$ in which $R^a$ and $R^b$ may be the same or different and each represents a hydrogen atom or a lower alkyl group or $R^a$ and $R^b$ may form a pyrrolidine ring together with the nitrogen atom to which $R^a$ and $R^b$ are bonded; a group —NH—$(CH_2)_m$—Z in which Z represents an amino group, one or both of the hydrogen atoms on the nitrogen atom of which may each be substituted by a lower alkyl group or a cyano group, and m stands for an integer of from 0 to 3; a group $NR^c(CH_2)_n$—OH in which $R^c$ represents a hydrogen atom or a lower alkyl group, and n stands for a natural number of from 1 to 4; a group —X—Y in which X represents S or NH, and Y represents a 2-imidazolin-2-yl, 2-imidazolyl, 1-methylimidazol-2-yl, 1,2,4-triazol-3-yl, 2-pyrimidyl or 2-benzimidazolyl group which may be substituted by one or more lower alkyl groups; or a ureido or thioureido group, one or more of the hydrogen atom(s) on one or both of the nitrogen atoms of which may each be substituted by a lower alkyl group, with the proviso that $R^1$ and $R^2$ are not a bromine atom and an amino group, respectively, at the same time; or a salt thereof.

2. The uracil derivative or salt thereof according to claim 1, wherein in the formula (1'), the group represented by $R^2$ is an amidinothio group, one or more of the hydrogen atom(s) on one or both of the nitrogen atoms of which may each be substituted by a lower alkyl group; a guanidino group, one or more of the hydrogen atom(s) on one, two or all of the nitrogen atoms of which may each be substituted by a lower alkyl or cyano group; or a (lower alkyl)amidino group.

3. The uracil derivative or salt thereof according to claim 1, wherein in the formula 1', the group represented by $R^2$ is selected from the group consisting of an amidinothio, $N^1$-methylamidinothio, $N^1,N^2$-dimethylamidinothio, 1-guanidino, 1-methylguanidino, 3-methylguanidino, 2,3-dimethylguanidino and an acetoamidino group.

4. The uracil derivative or salt thereof according to claim 2, wherein in the formula 1', the group represented by $R^2$ is selected from the group consisting of an amidinothio, $N^1$-methylamidinothio, $N^1,N^2$-dimethylamidinothio, 1-guanidino, 1-methylguanidino, 3-methylguanidino, 2,3-dimethylguanidino and an acetoamidino group.

5. The uracil derivative or salt thereof according to claim 1, wherein in the formula 1', the group represented by $R^1$ is selected from the group consisting of chlorine, bromine, and cyano, and the group represented by $R^2$ is an amidinothio or 1-guanidino group.

6. The uracil derivative or salt thereof according to claim 1, which is selected from the group consisting of 2-(5-chlorouracil-6-ylmethyl)-isothiourea hydrochloride, 2-(5-cyanouracil-6-ylmethyl)isothiourea hydrochloride and 5-chloro-6-(1-guanidino)methyluracil hydrochloride.

7. A pharmaceutical composition comprising:
a uracil derivative represented by the following formula (1):

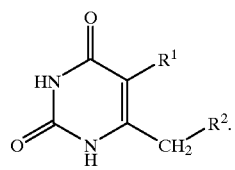

(1)

wherein $R^1$ is selected from the group consisting of chlorine, bromine, iodine, cyano and a lower alkyl group; and $R^2$ represents an amidinothio group, one or more of the hydrogen atom(s) on one or both of the nitrogen atoms of which may each be substituted by a lower alkyl group; a guanidino group, one or more of the hydrogen atom(s) on one, two or all of the nitrogen atoms of which may each be substituted by a lower alkyl or cyano group; a (lower alkyl)amidino group; a group —$CH_2N(R^a)R^b$ in which $R^a$ and $R^b$ may be the same or different and each represents a hydrogen atom or a lower alkyl group or $R^a$ and $R^b$ may form a pyrrolidine ring together with the nitrogen atom to which $R^a$ and $R^b$ are bonded; a group —NH—$(CH_2)_m$—Z in which Z represents an amino group, one or both of the hydrogen atoms on the nitrogen atom of which may each be substituted by a lower alkyl group or a cyano group, and m stands for an integer of from 0 to 3; a group $NR^c(CH_2)_n$—OH in which $R^c$ represents a hydrogen atom or a lower alkyl group, and n stands for a natural number of from 1 to 4; a group —X—Y in which X represents S or NH, and Y represents a 2-imidazolin-2-yl, 2-imidazolyl, 1-methylimidazol-2-yl, 1,2,4-triazol-3-yl, 2-pyrimidyl or 2-benzimidazolyl group which may be substituted by one or more lower alkyl groups; or a ureido or thioureido group, one or more of the hydrogen atom(s) on one or both of the nitrogen atoms of which may each be substituted by a lower alkyl group; or a salt thereof; and a pharmaceutically acceptable carrier.

8. The pharmaceutical composition according to claim 7, wherein in the formula (1), the group represented by $R^2$ is an amidinothio group, one or more of the hydrogen atom(s) on one or both of the nitrogen atoms of which may each by substituted by a lower alkyl group; a guanidino group, one or more of the hydrogen atom(s) on one, two or all of the nitrogen atoms of which may each by substituted by a lower alkyl or cyano group; or a (lower alkyl)amidino group.

9. The pharmaceutical composition according to claim 7, wherein in the formula (1), the group represented by $R^2$ is selected from the group consisting of an amidinothio, $N^1$-methylamidinothio, $N^1,N^2$-dimethyl-amidinothio, 1-guanidino, 1-methylguanidino, 3-methylguanidino, 2,3,-dimethylguanidino and an acetoamidino group.

10. The pharmaceutical composition according to claim 8, wherein in the formula (1), the group represented by $R^2$ is selected from the group consisting of an amidinothio, $N^1$-methylamidinothio, $N^1,N^2$-dimethyl-amidinothio, 1-guanidino, 1-methylguanidino, 3-methylguanidino, 2,3,-dimethylguanidino and an acetoamidino group.

11. The pharmaceutical composition according to claim 7, wherein in the formula (1), the group represented by $R^1$ is selected from the group consisting of chlorine, bromine, and cyano, and the group represented by $R^2$ is an amidinothio or 1-guanidino group.

12. The pharmaceutical composition according to claim 7, wherein the compound represented by the formula (1) is selected from the group consisting of 2-(5-chlorouracil-6-ylmethyl)isothiourea hydrochloride, 2-(5-cyanouracil-6-ylmethyl)isothiourea hydrochloride and 5-chloro-6-(1-guanidino)methyluracil hydrochloride.

13. A method for potentiating an antitumor effect of an antitumor agent containing a 2'-deoxypyrimidine nucleoside, which comprises administering to a patient an effective amount of a uracil derivative represented by the following formula (1):

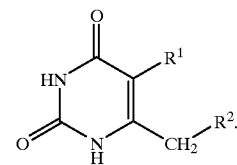

(1)

wherein $R^1$ is selected from the group consisting of chlorine, bromine, iodine, cyano and a lower alkyl group; and $R^2$ represents an amidinothio group, one or more of the hydrogen atom(s) on one or both of the nitrogen atoms of which may each be substituted by a lower alkyl group; a guanidino group, one or more of the hydrogen atom(s) on one, two or all of the nitrogen atoms of which may each be substituted by a lower alkyl or cyano group; a (lower alkyl)amidino group; a group —$CH_2N(R^a)R^b$ in which $R^a$ and $R^b$ may be the same or different and each represents a hydrogen atom or a lower alkyl group or $R^a$ and $R^b$ may form a pyrrolidine ring together with the nitrogen atom to which $R^a$ and $R^b$ are bonded; a group —NH—$(CH_2)_m$—Z in which Z represents an amino group, one or both of the hydrogen atoms on the nitrogen atom of which may each be substituted by a lower alkyl group, or a cyano group, and m stands for an integer of from 0 to 3; a group $NR^c(CH_2)_n$—OH in which $R^c$ represents a hydrogen atom or a lower alkyl group, and n stands for a natural number of from 1 to 4; a group —X—Y in which X represents S or NH, and Y represents a 2-imidazolin-2-yl, 2-imidazolyl, 1-methylimidazol-2-yl, 1,2,4-triazol-3-yl, 2-pyrimidyl or 2-benzimidazolyl group which may be substituted by one or more lower alkyl groups; or a ureido or thioureido group, one or more of the hydrogen atom(s) on one or both of the nitrogen atoms of which may each be substituted by a lower alkyl group; or a salt thereof.

14. A therapeutic method for treating cancer, which comprises administering to a patient in need of treatment an effective amount of a uracil derivative represented by the following formula

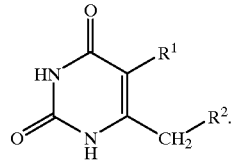

(1)

wherein $R^1$ is selected from the group consisting of chlorine, bromine, iodine, cyano and a lower alkyl group; and $R^2$ represents an amidinothio group, one or more of the hydrogen atom(s) on one or both of the nitrogen atoms of which may each be substituted by a lower alkyl group; a guanidino group, one or more of the hydrogen atom(s) on one, two or all of the nitrogen atoms of which may each be substituted by a lower alkyl or cyano group; a (lower alkyl)amidino group; a group —$CH_2N(R^a)R^b$ in which $R^a$ and $R^b$ may be the same or different and each represents a hydrogen atom or a lower alkyl group or $R^a$ and $R^b$ may form a pyrrolidine ring together with the nitrogen atom to which $R^a$ and $R^b$ are bonded; a group —NH—$(CH_2)_m$—Z in which Z represents an amino group, one or both of the hydrogen atoms on the nitrogen atom of which may each be substituted by a lower alkyl group or a cyano group, and m stands for an integer of from 0 to 3; a group $NR^c(CH_2)_n$—OH in which $R^c$ represents a hydrogen atom or a lower alkyl group, and n stands for a natural number of from 1 to 4; a group —X—Y in which X represents S or NH, and Y represents a 2-imidazolin-2-yl, 2-imidazolyl, 1-methylimidazol-2-yl, 1,2,4-triazol-3-yl, 2-pyrimidyl or 2-benzimidazolyl group which may be substituted by one or more lower alkyl groups; or a ureido or thioureido group, one or more of the hydrogen atom(s) on one or both of the nitrogen atoms of which may each be substituted by a lower alkyl group; or a salt thereof; and a 2'-deoxypyrimidine nucleoside.

* * * * *